United States Patent
Ellman et al.

(10) Patent No.: US 8,476,451 B2
(45) Date of Patent: Jul. 2, 2013

(54) TUBULYSIN D ANALOGUES

(75) Inventors: Jonathan A. Ellman, Oakland, CA (US); Andrew W. Patterson, Oakland, CA (US); Hillary Peltier, Jeanette, PA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/669,364

(22) PCT Filed: Jul. 21, 2008

(86) PCT No.: PCT/US2008/070677
§ 371 (c)(1),
(2), (4) Date: Aug. 4, 2010

(87) PCT Pub. No.: WO2009/134279
PCT Pub. Date: Nov. 5, 2009

(65) Prior Publication Data
US 2011/0021568 A1    Jan. 27, 2011

Related U.S. Application Data

(60) Provisional application No. 60/950,964, filed on Jul. 20, 2007, provisional application No. 61/048,902, filed on Apr. 29, 2008.

(51) Int. Cl.
*A61K 31/426* (2006.01)
*A61K 31/427* (2006.01)
*C07D 277/30* (2006.01)
*A01N 43/78* (2006.01)

(52) U.S. Cl.
USPC .......................... 548/200; 548/201; 514/365

(58) Field of Classification Search
USPC ................................................ 548/200, 201
See application file for complete search history.

(56) References Cited

U.S. PATENT DOCUMENTS 7,754,885 B2 *    7/2010  Hoefle et al. ................. 546/208
2005/0239713 A1  10/2005  Domling et al.
2011/0263650 A1 * 10/2011  Ellman et al. ................ 514/326

FOREIGN PATENT DOCUMENTS

WO    WO-2004/046170 A2 *  6/2004

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Golub et al., Science, vol. 286, Oct. 15, 1999, pp. 531-537.*
Steinmeiz et al., Angewandte Chemie International Edition, Sep. 2004, vol. 43, No. 37, pp. 4888-4892.*
Moss et al., Pure and Applied Chemistry, vol. 67, Nos. 8/9, pp. 1307-1310, 1320, 1321, 1340, 1341, (1995).*
Patterson et al., Chemistry—A European Journal, (Sep. 2007), 13(34), pp. 9534-9541.*
Peltier et al., Journal of the American Chemical Society, (Dec. 1, 2006), 128(50), pp. 16018-16019.*
Soreide et al., Discovery Medicine, Nov. 17, 2011, 12(66), pp. 393-404.*
de Wijkerslooth et al., The Netherlands Journal of Medicine, Mar. 2011, 69(3), pp. 112-119.*

* cited by examiner

*Primary Examiner* — Laura L. Stockton
(74) *Attorney, Agent, or Firm* — Morgan, Lewis & Bockius LLP; Jeffrey S. Mann

(57) ABSTRACT

The present invention provides novel tubulysin analogues, methods of making and methods of using such analogues and conjugates thereof. The compounds of the invention are highly potent cell-growth inhibitors have been developed that are smaller and considerably more stable than tubulysin D.

24 Claims, 1 Drawing Sheet

| Structure | MW |
|---|---|
| 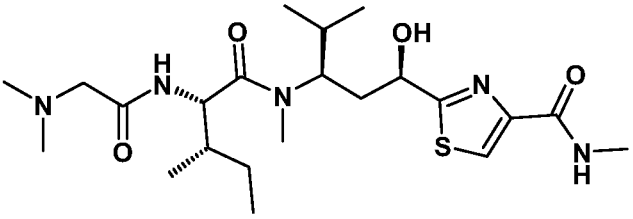 | 469.65 |
| 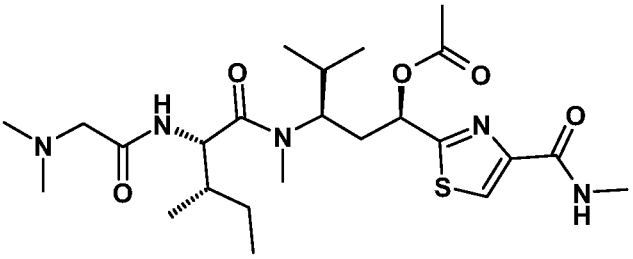 | 511.69 |
| 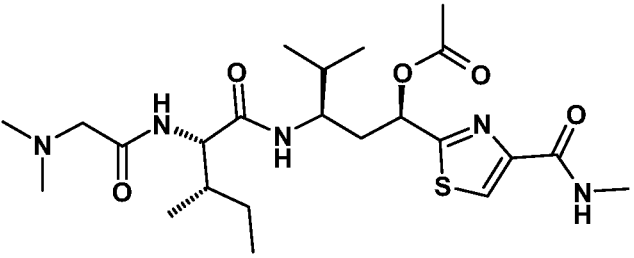 | 497.66 |
| 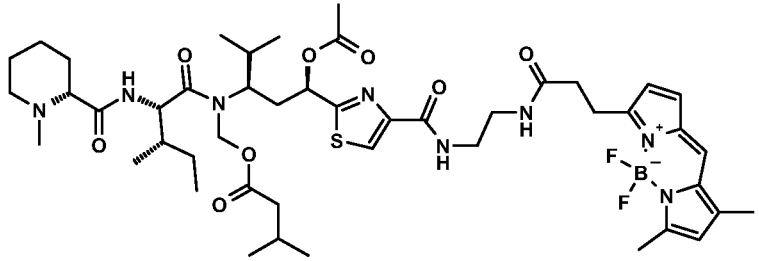 | 954.99 |

TUBULYSIN D ANALOGUES

CROSS-REFERENCE TO RELATED APPLICATIONS

This application is an international filing under the Patent Cooperation Treaty of U.S. Provisional Application No. 60/950,964 filed Jul. 20, 2007 and No. 61/048,902 filed Apr. 29, 2008, the disclosure of each of which is incorporated herein by reference in its entirety for all purposes.

STATEMENT AS TO RIGHTS TO INVENTIONS MADE UNDER FEDERALLY SPONSORED RESEARCH AND DEVELOPMENT

This work was partially supported by grants from the National Science Foundation (CHE-0446173). The Government has certain rights in the subject matter disclosed herein.

FIELD OF THE INVENTION

This invention relates to analogues of tubulysin D, conjugates of such analogues, and methods of using the analogues and the conjugates thereof to arrest or retard cell growth and/or development.

BACKGROUND OF THE INVENTION

The tubulysins, first isolated by the Höfle/Reichenbach group from myxobacterial cultures (F. Sasse, H. Steinmetz, G. Höfle, H. Reichenbach, *J. Antibiot.* 2000, 53, 879-885), are exceptionally potent cell-growth inhibitors that act by inhibiting tubulin polymerization and thereby induce apoptosis. (M. W. Khalil, F. Sasse, H. Lünsdorf, Y. A. Elnakady, H. Reichenbach, *ChemBioChem,* 2006, 7, 678-683; and G. Kaur, M. Hollingshead, S. Holbeck, V. Schauer-Vukašinović, R. F. Camalier, A. Dömling, S. Agarwal, *Biochem. J.* 2006, 396, 235-242). The tubulysins, of which tubulysin D is the most potent, have activity that exceeds all almost all other tubulin modifiers including, the epothilones, vinblastine, and paclitaxel (Taxol), by 20- to 1000-fold. (H. Steinmetz, N. Glaser, E. Herdtweck, F. Sasse, H. Reichenbach, G. Höfle, *Angew. Chem.* 2004, 116, 4996-5000; H. Steinmetz, N. Glaser, E. Herdtweck, F. Sasse, H. Reichenbach, G. Höfle, *Angew. Chem. Int. Ed.* 2004, 43, 4888-4892; and G. Höfle, N. Glaser, T. Leibold, U. Karama, F. Sasse, H. Steinmetz, *Pure and Applied Chemistry* 2003, 75,167-178). Paclitaxel and vinblastine are current treatments for a variety of cancers, and epothilone derivatives are under active evaluation in clinical trials. Synthetic derivatives of tubulysin D would provide essential information about the mechanism of inhibition and key binding interactions, and could have superior properties as anticancer agents either as isolated entities or as chemical warheads on targeted antibodies or ligands.

Tubulysin D (1) is a complex tetrapeptide that can be divided into four regions as shown in Formula I: Mep (D-N-methyl pipecolinic acid), Ile (L-isoleucine), Tuv (tubuvaline), and Tup (tubuphenylalanine). All of the more potent derivatives of tubulysin, including tubulysin D, also incorporate the interesting O-acyl N,O-acetal functionality, which has rarely been observed in natural products. This reactive functionality is documented to be quite labile to both acidic and basic reaction conditions, and therefore may play a key role in the function of the tubulysins. (J. Iley, R. Moreira, T. Calheiros, E. Mendes, *Pharm. Res.* 1997, 14, 1634-1639).

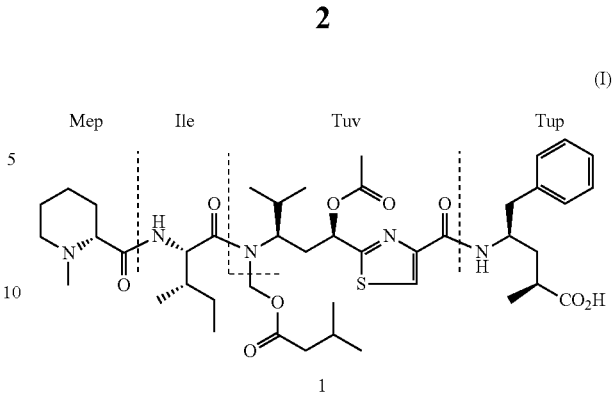

(I)

Recently, the total synthesis of tubulysin D was reported, which represents the first synthesis of any member of the tubulysin family that incorporates the O-acyl N,O-acetal functionality. (H. M. Peltier, J. P. McMahon, A. W. Patterson, J. A. Ellman, *J. Am. Chem. Soc.* 2006, 128, 16018-16019).

A cost-efficient, scalable method for the synthesis of tubulysin and tubulysin analogues would be a significant addition to the array of available chemistries. Furthermore, tubulysin analogues that are structurally more simple and approximately as bioactive as the naturally occurring tubulysins would provide for ease of access to important cell growth inhibitors. The current invention addresses this and other needs.

SUMMARY OF THE INVENTION

This invention provides a new class of tubulysin analogues. It has been discovered that they have a lower molecular weight and are considerably more stable than tubulysin, while maintaining the majority of tubulin polymerization inhibitory activity. The invention also provides tubulysin analogues of use in forming conjugates between the analogues and one or more binding partner.

Upon examination of the Tup position at the C-terminus of tubulysin D it was found that a wide range of modifications are tolerated. Analogues designed to retain only the phenethyl (2) or γ-carboxy (3) group showed cytoxicity comparable to the parent tubulysin. Even greatly simplified N-methyl derivatives (4) and truncated tripeptide analogues (5) maintained good activity. The considerable tolerance at this site for large and small as well as hydrophobic and hydrophilic functionality is of considerable significance because it allows this site to act as a locus for the attachment of various modifying agents to, e.g., increase or reduce the molecular weight, enhance pharmacokinetics, modulate compound binding and toxicity, target the compound to specific tissues by using, e.g., targeted antibodies. The site also serves as an attachment point for the incorporation of detectable species and probe molecules such as fluorescent agents.

Examination of the Mep position at the N-terminus of the natural product established the importance of maintaining a basic amine at this position. Removal of the Mep group (8) and replacement of the Mep group with a simple acetyl group (7) caused a drastic decrease in activity. However, compounds in which the amine functionality is retained (e.g., compounds such as 6 which retain the tertiary amine functionality), are essentially equipotent with tubulysin D. In addition to defining the importance of the basic amine, the simplified nature and lower molecular weight of the analogues of the invention in comparison to that of tubulysin D is noteworthy.

Thus, the current invention provides a compound having a structure according to Formula II:

(II)

[Chemical structure of Formula II showing R¹, R⁶ᵃ, R², R³, Me, Me, O, OR³, N, Y, S groups]

In Formula II, $R^1$ is a nitrogen containing moiety such as an amine, an amide, an azide, a hydrazide or a hydrazone. The nitrogen containing moiety is optionally substituted with a member selected from H, substituted or unsubstituted alkyl, substituted or unsubstituted heteroalkyl, substituted or unsubstituted aryl, substituted or unsubstituted heteroaryl and substituted or unsubstituted heteroarylalkyl, as defined herein. $R^2$ is H, substituted or unsubstituted alkyl or substituted or unsubstituted heteroalkyl, $R^3$ is H, substituted or unsubstituted alkyl, or substituted or unsubstituted heteroalkyl. $R^3$ can also be an acyl group (C(O)R), as defined herein. The "R" substituent on the acyl group is preferably selected from substituted or unsubstituted alkyl, substituted or unsubstituted heteroalkyl, substituted or unsubstituted aryl, substituted or unsubstituted heteroaryl, substituted or unsubstituted heterocycloalkyl and other members of the group of substituents referred to herein as "alkyl group substituents." Exemplary acyl moieties include carboxylic acids, carboxylic acid esters, carboxamides, ketones, aldehydes and the like. $R^{6a}$ is H, substituted or unsubstituted alkyl or substituted or unsubstituted heteroalkyl.

Exemplary groups for Y include, but are not limited to $(CH_2)_n COOR^4$, $(CH_2)_n OR^4$; and $(CH_2)_n C(O)NR^4 R^5$ in which n is an integer from 0 to 5. $R^4$ and $R^5$ are independently selected from H, substituted or unsubstituted alkyl and substituted or unsubstituted heteroalkyl. When Y is $(CH_2)_n COOR^4$, $R^4$ is optionally a negative charge forming a salt with M+, in which M+ is an organic or inorganic ion, providing a compound with the moiety $(CH_2)_n COO^- M^+$. $OR^4$ is also optionally a leaving group as this term is commonly recognized in the art of organic synthesis.

In an exemplary embodiment, either or both $R^1$ and $R^{6a}$ include a residue of an amino acid or peptide. In another embodiment, the residue of the amino acid or peptide is linked to the remainder of the molecule by the group —C(O)NH—, wherein —C(O) of this moiety is preferably derived from a carboxylic acid of the amino acid.

Compounds according to Formula II can be used as components of reactions forming conjugates with other molecules, e.g., carrier molecules.

Also provided is a compound according to Formula IIa:

(IIa)

[Chemical structure of Formula IIa showing R⁶ᶜ, R⁶ᵇ, R⁶ᵃ, R², Me, Me, OR³, N, S, (CH₂)ₙ—COX groups]

In exemplary compounds according to Formula IIa, X is $OR^x$, in which $R^x$ is H, or $OR^x$ is $O^- M^+$, in which $M^+$ is an organic or inorganic anion. $OR^x$ can also be a leaving group as this term is commonly recognized in the art of synthetic organic chemistry. Exemplary moieties for $R^x$ when $OR^1$ is a leaving group include substituted or unsubstituted alkyl, substituted or unsubstituted heteroaryl, substituted or unsubstituted aryl, and substituted or unsubstituted heteroaryl acyl. As will be appreciated by those of skill $OR^x$ can itself be converted into a leaving group, e.g., a halogen. $R^{6b}$ and $R^{6c}$ are independently selected from H, substituted or unsubstituted alkyl and substituted or unsubstituted heteroalkyl. The other moieties have the identities set forth in the context of Formula II. Exemplary compounds according to Formula IIa can be utilized as a starting material for conjugates with one or more binding partners The invention includes pharmaceutically acceptable salts, hydrates, solvates, prodrugs, metabolites and polymorphs of the compounds according to Formula II, Formula IIa and of conjugates formed utilizing a compound according to Formula II or Formula IIa.

Also provided are pharmaceutical formulations including a compound of the invention, or a conjugate formed utilizing a compound of the invention, and one or more pharmaceutically acceptable diluent, excipient, carrier and the like.

In another aspect, the present invention provides a method of arresting or inhibiting cell growth and/or development. The method includes contacting a cell with a compound of the invention, or a conjugate formed using a compound of the invention, in an amount effective to arrest or inhibit cell growth and/or development. In a preferred embodiment, the cell that is treated is undergoing or is prone to undergoing unnatural growth or development, e.g., hyperplasia, cancer and the like.

In a further aspect, the invention provides a method of treating a disease by arresting or inhibiting the growth and/or development of a cell that is implicated in the disease. The method included administering to a subject in need of treatment a therapeutically effective amount of a composition or conjugate of the invention.

Additional objects, advantages and embodiments of the present invention are set forth in the detailed description that follows.

BRIEF DESCRIPTION OF THE DRAWINGS

FIG. 1 is a table of exemplary tubulysin analogues of the invention.

DETAILED DESCRIPTION OF THE INVENTION

Introduction

The present invention provides a series of analogues of tubulysin D containing variations at the Tup, Mep, and N,O-acetal positions that has for the first time established the essential features of these regions of the natural product necessary for biological activity against a series of human and animal cancer cell lines. The biological data indicates that a wide range of modifications at the Tup position are well-tolerated indicating that this is a key location for conjugation to antibodies or for the incorporation of fluorescent and other probe molecules. The biological data also indicates that while a basic amine in the Mep region of tubulysin is necessary for biological activity, very simple and low molecular weight substituents, e.g., 6, are acceptable at this site. Notably, neither of the most labile sites in the natural product, the O-acetyl group and the O-acyl N,O-acetal, are necessary for biological activity. This finding enables the design of highly potent tubulysin analogues that are of considerably greater stability than the natural product.

Also provided are tubulysin derivatives that are functionalized to allow their convenient conjugation to one or more binding partner.

Definitions

Where substituent groups are specified by their conventional chemical formulae, written from left to right, they optionally encompass substituents resulting from writing the structure from right to left, e.g., —CH$_2$O— optionally also recites —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" with the difference that the heteroalkyl group, in order to qualify as an alkyl group, is linked to the remainder of the molecule through a carbon atom. Alkyl groups that are limited to hydrocarbon groups are termed "homoalkyl".

The term "alkenyl" by itself or as part of another substituent is used in its conventional sense, and refers to a radical derived from an alkene, as exemplified, but not limited by, substituted or unsubstituted vinyl and substituted or unsubstituted propenyl. Typically, an alkenyl group will have from 1 to 24 carbon atoms, with those groups having from 1 to 10 carbon atoms being generally preferred.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent may be attached to the remainder of the molecule directly or through a linker, wherein the linker is preferably alkylene. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) optionally includes both aryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") optionally include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), boron (B) and phosphorus (P).

The symbol "R" is a general abbreviation that represents a substituent group, e.g., one that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

"Peptide" refers to a polymer in which the monomers are "amino acids" and are joined together through amide bonds, alternatively referred to as a polypeptide. When the amino acids are α-amino acids, either the L-optical isomer or the D-optical isomer can be used. Additionally, non-standard amino acids, e.g., amino acids that are not gene-encoded are also of use in the compounds of the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Amino acid residue" refers to a moiety formed by replacement of one or more atom of an amino acid with a covalent bond linking the amino acid residue to the remainder of the molecule. The term amino acid residue also includes peptidyl residues, e.g., those residues containing more than one amino acid. A residue of any amino acid is of use in the compounds of the present invention.

The standard amino acids of use in the present invention include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Aside from the twenty standard amino acids, there are a vast number of "nonstandard amino acids" of use in the compounds of the invention. Two of these can be encoded in the genetic code, but are rather rare in proteins. Selenocysteine is incorporated into some proteins and pyrrolysine is used by some methanogenic bacteria in enzymes that they use to produce methane. Further examples of nonstandard amino acids include lanthionine, 2-aminoisobutyric acid, dehydroalanine and the neurotransmitter gamma-aminobutyric acid. Nonstandard amino acids often occur as intermediates in the metabolic pathways for standard amino acids—for example ornithine and citrulline occur in the urea cycle, part of amino acid catabolism. Nonstandard amino acids are also formed through modifications to standard amino acids. For example, homocysteine is formed through the transsulfuration pathway or by the demethylation of methionine via the intermediate metabolite S-adenosyl methionine, while dopamine is synthesized from 1-DOPA, and hydroxyproline is made by a posttranslational modification of proline. Other non-standard amino acids of use in the compounds of the invention include the β-amino acids. Additional non-standard amino acids are β-alanine, phenylglycine and homoarginine. An "amino acid residue" is a moiety formed by removal of one or more atom from an "amino acid." Exemplary amino acid residues are joined to the remainder of the molecule of which they are a part through an acyl bond (e.g., one formed between the carboxy terminus or side chain carboxylate and an amine, alcohol, sulfhydryl and the like), an amine or amide bond (e.g., formed through the amino terminus or side chain amine), an ether or thioether (e.g., formed through a side chain alcohol or thiol, respectively), and the like.

The phrase "therapeutically effective amount" as used herein means that amount of a compound, material, or composition comprising a compound of the present invention which is effective for producing some desired therapeutic effect by inhibition of DAAO in at least a sub-population of cells in an animal and thereby blocking the biological consequences of that pathway in the treated cells, at a reasonable benefit/risk ratio applicable to any medical treatment.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent.

Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When a residue (such as $R^4$ in this application) is defined as "O$^-$", then the formula is meant to optionally include an organic or inorganic cationic counterion. Preferably, the resulting salt form of the compound is pharmaceutically acceptable.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. For instance, prodrugs for carboxylic acid analogs of the invention include a variety of esters. In an exemplary embodiment, the pharmaceutical compositions of the invention include a carboxylic acid ester. In another exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

In the context of the present invention, preferred compounds having activity as growth inhibitors are those displaying 50% inhibition of cell growth ($IC_{50}$) at a concentration of not higher than about 150 nM, preferably, not higher than about 10 nM, more preferably not higher than about 5 nM and most preferably not higher than about 1 nM.

"Carrier molecule," as used herein refers to species to which the compounds of the invention are conjugated through a covalent bond formed by reaction of a reactive functional group on the compound of the invention and a reactive functional group of complementary reactivity on the carrier molecule. Exemplary classes of carrier molecules include proteins, nucleic acids, detectable agents, therapeutic agents and both water-soluble and water-insoluble polymers. Exemplary proteins include antibodies, which are of use to target the conjugates of the invention to selected tissues. Exemplary nucleic acids include nucleotides and nucleoside, nucleotide and nucleoside mimetics, and oligonucleotides containing both naturally occurring and unnatural base monomers. Exemplary detectable agents include fluorophores, mass tags and radioactive agents. Exemplary therapeutics include anticancer chemotherapeutic agents, anti-inflammatory agents and hormones. Exemplary water-soluble polymers include amino acid polymers (e.g., poly-lysine), saccharides (e.g., dextraon, hydroxyethyl starch), and branched synthetic polymers (e.g., dendrimers). Exemplary water-insoluble polymers include amino acid polymers (e.g., polyglutamic acid), saccharides (e.g., starch, chitin), and branched synthetic polymers (e.g., dendrimers. Each above-recited polymer class further includes copolymers with every other class.

The Compositions

The present invention provides tubulysin analogues having a structure according to Formulae II-VIII:

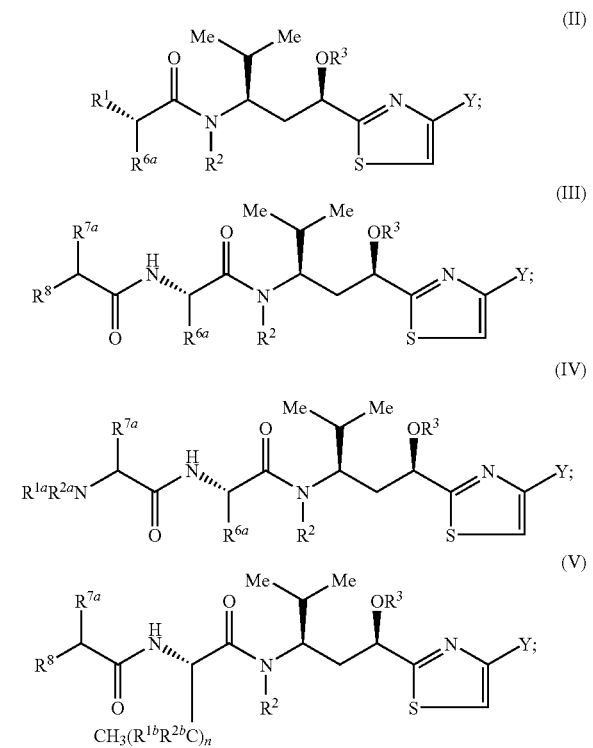

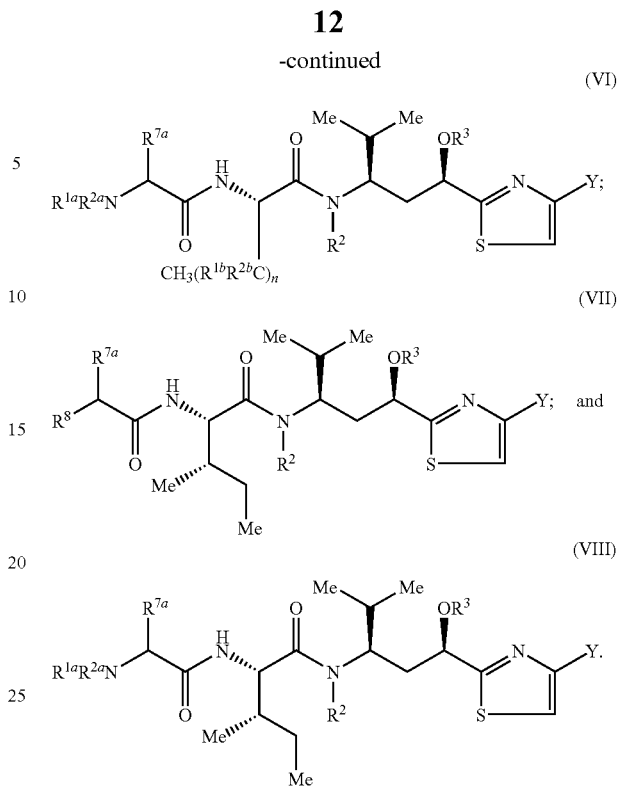

In each of the above formulae, $R^1$ is a nitrogen containing moiety such as an amine, an amide, an azide, a hydrazide or a hydrazone. $R^2$ is H, substituted or unsubstituted alkyl or substituted or unsubstituted heteroalkyl. $R^3$ is H, substituted or unsubstituted alkyl, or substituted or unsubstituted heteroalkyl. $R^{6a}$, $R^{7a}$ and $R^8$ are independently selected from H, substituted or unsubstituted alkyl and substituted or unsubstituted heteroalkyl.

The amine substituents, $R^{1a}$ and $R^{2a}$ are independently selected from H, substituted or unsubstituted alkyl, substituted or unsubstituted heteroalkyl, substituted or unsubstituted aryl, substituted or unsubstituted heteroaryl and substituted or unsubstituted heteroarylalkyl. In an exemplary embodiment, either or both $R^{1a}$ and $R^{2a}$, together with the nitrogen to which it is attached are joined into a ring with $R^{7a}$. Preferred rings are 4-8-member, preferably 5-6-member heterocycloalkyl rings with from 1-3, preferably from 1-2 heteroatoms.

$R^{1b}$ and $R^{2b}$ are independently selected from H and other "alkyl group substituents" as defined hereinabove. $R^{1b}$ and $R^{2b}$, together with the carbon to which they are bound are optionally joined into a substituted or unsubstituted cycloalkyl or heterocycloalkyl ring. Preferred rings are 4-8-member, preferably 5-6-member rings with from 0-3, preferably from 0-2 heteroatoms.

Exemplary groups for Y include, but are not limited to, $(CH_2)_n COOR^4$, $(CH_2)$—$OR^4$; $(CH_2)_n NR^4 R^5$ and $(CH_2)_n C(O)NR^4 R^5$ in which n is an integer from 0 to 10, preferably 0-5, and more preferably 0-2, and $R^4$ and $R^5$ are independently selected from H, substituted or unsubstituted alkyl and substituted or unsubstituted heteroalkyl.

When Y is $(CH_2)_n COOR^4$, $R^4$ is optionally a negative charge, forming a s salt with M+, in which M+ is an organic or inorganic ion, providing a compound with the moiety $(CH_2)_n COO^- M^+$. In each compound including $OR^4$ this moiety is also optionally a leaving group as this term is commonly recognized in the art of organic synthesis. Exemplary leaving groups include, but are not limited to, imidazolides, active esters, e.g., N-hydroxysuccinimide, p-nitrophenol, and other art-recognized leaving groups. The index "n" is as set forth above.

As discussed below, Y may also be a locus for conjugating another species to the tubulysin analogue core, e.g., a polymer, a peptide, polypeptide, protein, including antibodies and antibody fragments. Agents that target the tubulysin analogue to a particular tissue are presently preferred conjugation partners for the analogues. In those embodiments in which Y is a locus for conjugation with a modifying group or a modifying group-linker cassette, it will be apparent to those of skill that the substitution on the atom to which the modifying group or cassette is attached is altered from those shown above, e.g., $(CH_2)_nOH$, is then $(CH_2)_nO-M$ or $(CH_2)_nO-L-M$. Similarly, $(CH_2)_nNH_2$, is then $(CH_2)_nNH-M$ or $(CH_2)_nNH-L-M$, and the like, in which M and L represent the modifying moiety and linker, respectively.

In an exemplary embodiment, either or both $R^1$ and $R^{6a}$ include a residue of an amino acid or peptide. In another embodiment, the residue of the amino acid or peptide is linked to the remainder of the molecule by the group —C(O)NH—.

The invention includes pharmaceutically acceptable salts, hydrates, solvates, prodrugs, metabolites and polymorphs of the compounds according to the formulae above and the derivatives discussed below.

In an exemplary embodiment, $R^1$ is selected from substituted or unsubstituted $C_1$-$C_4$ straight-chain or branched-chain alkyl, or an acyl moiety. In another exemplary embodiment, $R^1$ includes the moiety:

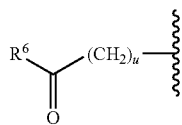

in which $R^6$ is saturated or unsaturated, substituted or unsubstituted heterocycloalkyl or heteroaryl. A preferred heterocycloalkyl or heteroaryl moiety contains at least one nitrogen atom. A further preferred heterocycloalkyl or heteroaryl moiety is a 5- or 6-membered ring. The index u is an integer from 0 to 4.

$R^1$ can be the NH-MEP moiety, with the proviso that the resulting structure is not tubulysin D.

In an exemplary embodiment, $R^2$ is a substituted or unsubstituted $C_1$-$C_4$ alkyl or heteroalkyl moiety. Substituted or unsubstituted methyl and substituted or unsubstituted ethyl are presently preferred. In another exemplary embodiment, $R^2$ is the native $CH_2$—O acyl nitrogen substituent moiety of the Tuv subunit, with the proviso that resulting structure is not tubulysin D.

In another exemplary embodiment, $R^3$ is selected from substituted or unsubstituted $C_1$-$C_4$ straight-chain or branched-chain alkyl, or an acyl moiety. In another exemplary embodiment, $R^1$ is:

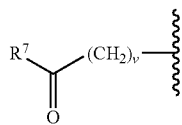

in which $R^7$ is saturated or unsaturated, substituted or unsubstituted alkyl or heteroalkyl moiety. Presently preferred alkyl and heteroalkyl moieties have from one to four members, e.g., a $C_1$-$C_4$ hydrocarbyl moiety. The index v is an integer from 0 to 4. $R^3$ can also be the acetyl moiety native to tubulysin D, with the proviso that the resulting structure is not tubulysin D.

In a further exemplary embodiment, one or both of $R^4$ and $R^5$ is substituted or unsubstituted alkyl or substituted or unsubstituted heteroalkyl, including an alkyl that is substituted by one or more carbonyl-containing moieties, e.g., amide, urethane, ester, etc. In an exemplary embodiment one or both of $R^4$ and $R^5$ is a linker arm between the tubulysin analogue core and a modifying moiety as discussed herein. Thus, for example, compounds according to Formula VII and VIII are within the scope of the invention:

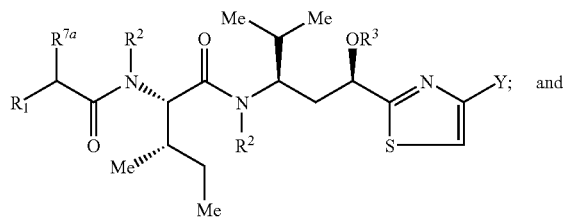

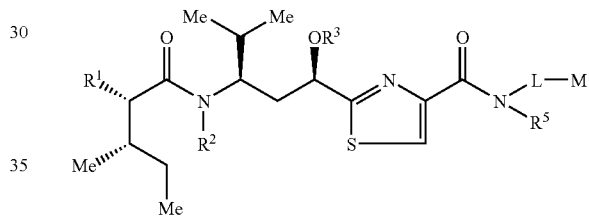

in which L represents a linker, which can be a bond ("zero-order"), or it can be formed through one of the many art-recognized hetero- and homo-bifunctional cross-linking agents that are commercially available or readily accessible to those of skill in the art. In an exemplary embodiment, L is a $C_1$-$C_{10}$, preferably a $C_1$-$C_6$ and more preferably a $C_1$-$C_4$ alkyl or heteroalkyl linker. In another exemplary embodiment, L is linked to M through an ether, an amide, an ester or an amine linkage; thus, L-M comprises one of these moieties.

In another exemplary embodiment, $R^4$ is the Tup moiety, absent the nitrogen, the Tup moiety being attached to the nitrogen of Formula II, with the proviso that the resulting structure is not tubulysin D. Similarly, $R^5$ can be hydrogen provided the resulting structure is other than tubulysin D.

In an exemplary embodiment, one or more of $R^1$-$R^4$ is functionalized either through a bond or through a linker with a modifying moiety or group as described hereinbelow.

Analogues 2-5 were designed to probe the Tup position at the C-terminus of the peptide natural product, while analogues 6-8 were designed to probe the Mep position at the N-terminus. Analogues 9 and 10 were designed to test the importance of the two most labile sites in the molecule. Analogue 9 serves to test the importance of the acetyl group present in the tubulysins. In contrast 10, which incorporates a methyl group in place of the reactive O-acyl N,O-acetal, like the natural product is still be able to access both cis- and trans-amide conformations because 10 retains the tertiary amide at the site of modification.

Compounds 2-10 were assayed against established mammalian cell lines, including cancer cells measuring inhibition of cell growth by an MTT assay (F. Sasse, H. Steinmetz, G. Höfle, H. Reichenbach, *J. Antibiot.* 2000, 53, 879-885. See, Table 1. The activities of the tubulysin analogues varied from 0.05-120 ng/mL in L929 mouse fibroblast cells, with a number of simplified analogues maintaining significant activity.

Upon examination of the Tup position at the C-terminus of tubulysin D (2-5), it was found that a wide range of modifications were tolerated (Tables 1 and 2). Analogues designed to retain only the phenethyl or γ-carboxy group showed comparable cytoxicity. Even the greatly simplified N-methyl derivative 4 and the truncated tripeptide 5 maintained good activity. The considerable tolerance at this site for large and small as well as hydrophobic and hydrophilic functionality is of considerable significance because it provides a site appropriate for attachment in the design of conjugates, e.g., targeted antibodies and for the incorporation of probe molecules, e.g., fluorescent agents.

Examination of the Mep position at the N-terminus of the natural product established the importance of maintaining a basic amine at this position. Removal of the Mep group (8) and replacement of the Mep group with a simple acetyl group (7) caused a drastic decrease in activity (Table 2). However, compound 6, which retains the tertiary amine functionality, was essentially equipotent with tubulysin D. In addition to defining the importance of the basic amine, the simplified nature and lower molecular weight of the N,N-dimethyl glycine present in 6 is also noteworthy.

TABLE 1

Tubulysin analogues 2-10.

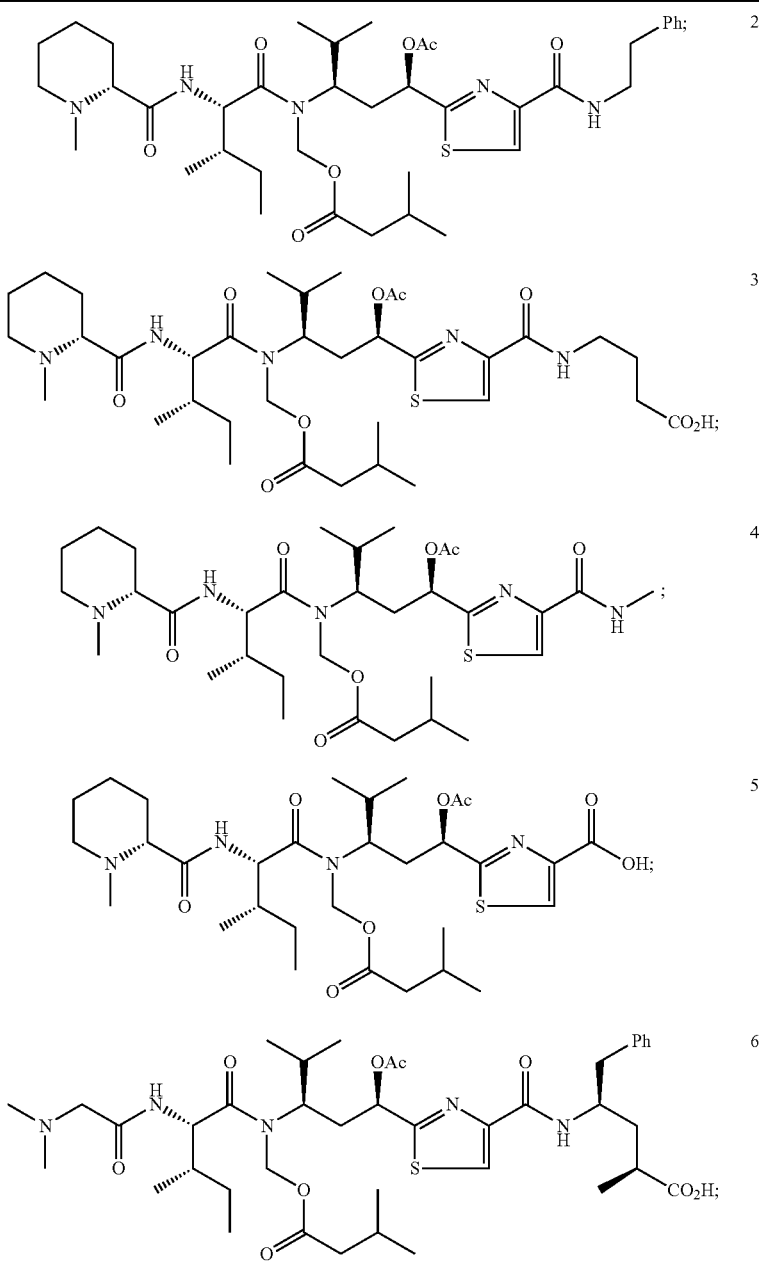

TABLE 1-continued

Tubulysin analogues 2-10.

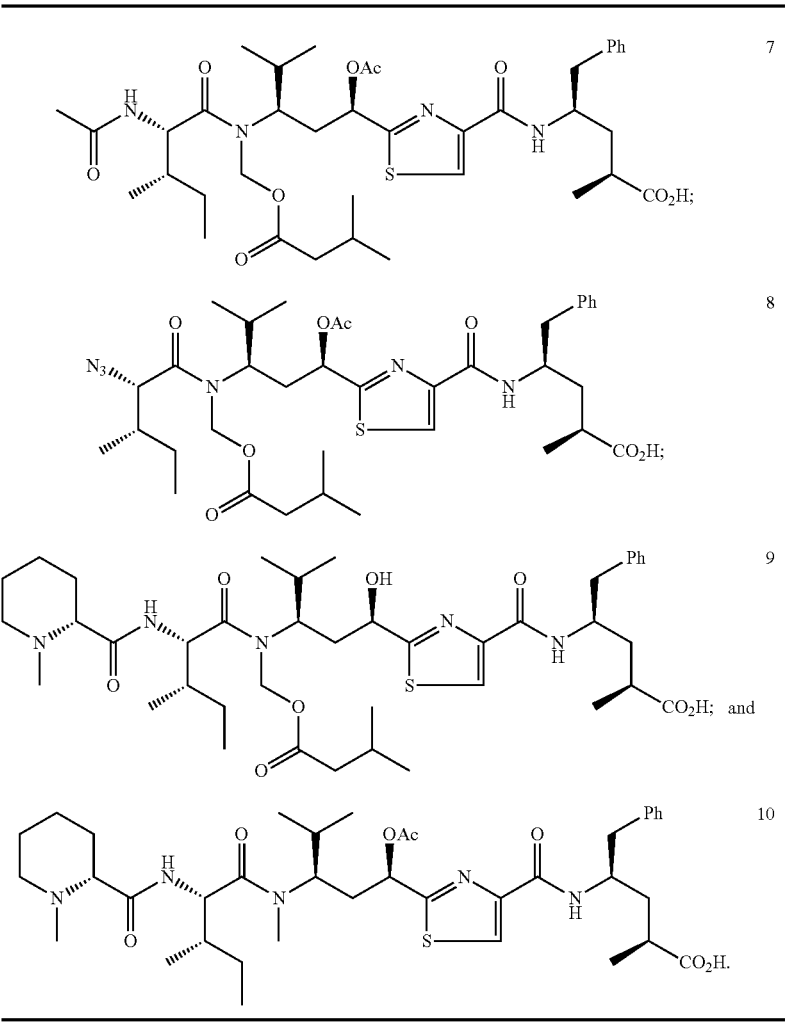

The activities observed for analogues 9 and 10 were most surprising. Analogue 9 showed a minimal drop in cytotoxicity relative to the natural product demonstrating that the O-acetyl group is not important for activity. The high cytotoxicity of 10, which is only 4-fold less active than tubulysin D, is even more surprising, and clearly indicates that the N,O-acetal is not necessary for cytoxicity.

TABLE 2

Biological activity of compounds 1-11.

| Analogue | IC$_{50}$ (ng/mL) L929[a] | SW-480[b] | KB-3-1[c] |
|---|---|---|---|
| 1 (Tub D)[d] | 0.056[e] | 0.022 | 0.070[f] |
| 2 | 0.24 | 0.30 | 0.25 |
| 3 | 3.5 | 0.91 | 1.8 |
| 4 | 0.30 | 0.35 | 0.22 |
| 5 | 2.2 | 0.35 | 1.5 |
| 6 | 0.040[g] | 0.010 | 0.029 |
| 7 | 120 | 15 | 80 |
| 8 | 45 | 8.8 | 40 |
| 9 | 0.25 | 0.057 | 0.22 |
| 10 | 0.23[h] | 0.016[g] | 0.13[g] |
| 11 | 1.7 | 0.50 | 1.2 |

[a]Mouse fibroblasts (DSMZ ACC 2).
[b]Human colon adenocarcinoma (ATCC CCL-228).
[c]Human cervix carcinoma (DSMZ ACC 158).
[d]Synthetic tubulysin D prepared previously.
[e]The IC$_{50}$ of isolated tubulysin D was previously determined to be 0.01-0.03 ng/mL with cell line L929.
[f]The IC$_{50}$ of isolated tubulysin D was previously determined to be 0.02 ng/mL with cell line KB-3-1.
[g]Average of two experiments.
[h]Average of four experiments.

To discern whether the structure-activity relationships observed for the analogue series were additive, analogue 11, which combines the truncations present in both analogues 4 and 10, was also prepared. Potent cytotoxicity (2.0 ng/mL) was observed for 11 (Table 2). This result is particularly surprising because 11 at 551 Da is considerably lower in molecular weight than tubulysin D (827 Da). In addition, analogue 11 incorporates the stable N-methyl group in place of the reactive O-acyl N,O-acetal functionality.

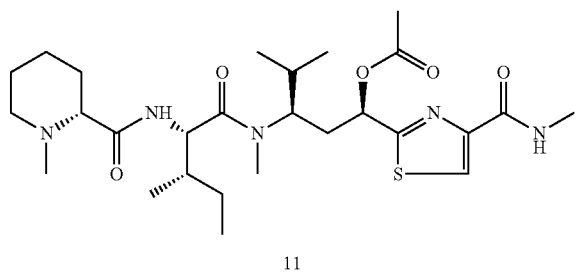

11

IC$_{50}$ = 1.7 ng/mL
MW = 551 Da

Analogues can be tested against human colon and cervix cancer lines to determine their activity. For example, the analogues set forth above were analyzed in human colon and cervix cancer lines, with structure-activity relationships that largely parallel SAR for the L929 cell line. The activities of analogue 6, which possesses a Mep-modification, and analogue 10, which lacks the NO-acetal, in the colon cancer cell line SW-480 were also notable, with both analogues proving to be more active than tubulysin D.

To check for the mode of action of the analogues, PtK$_2$ potoroo cells were incubated with the analogues at concentrations above the IC$_{50}$ with L929, and stained for microtubule cytoskeleton by immunofluorescence methods after 18 hours. In each case we observed a disturbance in the microtubule system, either an interference with the microtubular network in non-dividing cells or abnormal mitotic spindles in dividing cells. These results show that the activity of all of the analogues can be attributed to an action on the tubulin/microtubule system, and is not a result of nonspecific cytotoxicity.

The synthesis of the aforementioned analogues 2-11 was accomplished in a highly efficient manner. Analogues 2-5 were prepared from intermediate 12 (Scheme 1), previously reported in the synthesis of tubulysin D. Activation of the acid as the pentafluorophenyl ester followed by addition of phenethylamine, 4-aminobutyric acid, or methylamine hydrochloride provided amides 13a-13e, respectively. Acetylation of the Tuv alcohol then provided analogues 2-4. Compound 5, which is terminated by the Tuv carboxylic acid, was directly prepared by acetylation of alcohol 12 (Scheme 1).

Scheme 1. Preparation of 3-6.

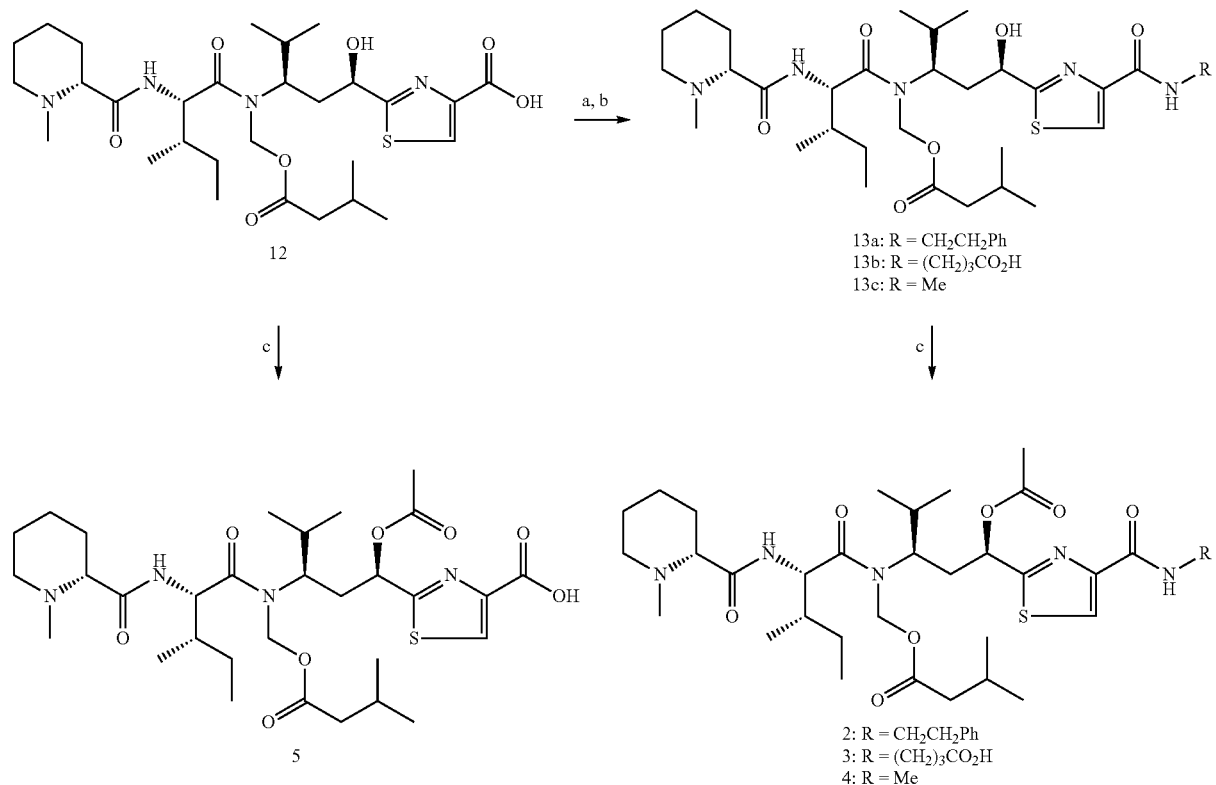

Reagents and conditions: a) pentafluorophenol, 1,3-diisopropylcarbodiimide, CH$_2$Cl$_2$; b) 2-phenylethylamine, 4-aminobutyric acid, or methylamine hydrochloride, i-Pr$_2$EtN, DMF, 49% (13a), 70% (13b), or 68% (13c) yield for two steps; c) Ac$_2$O, pyridine, then (for 4 and 6) H$_2$O/dioxane, 99% (3), 81% (4), 90% (5), or 97% (6).

For compounds 6-8 in which Mep at the N-termini has been replaced, an earlier azido intermediate in the synthesis of tubulysin D (14) was used as the common precursor. Silyl ether deprotection and then selective cleavage of the methyl ester over the reactive O-acyl N,O-acetal with Bu$_3$SnOH provided acid 16 (Scheme 2). Activation of the carboxylic acid as the pentafluorophenyl ester followed by addition of tubuphenylalanine hydrochloride (17) and acetylation of the Tuv alcohol afforded analogue 8. This analogue also serves as the penultimate intermediate to analogues 6 and 7, which were prepared by reduction of the azide in the presence of the pentafluorophenyl ester of N,N-dimethylglycine (18) or acetic acid (19), respectively.

Scheme 2. Preparation of 7-9.

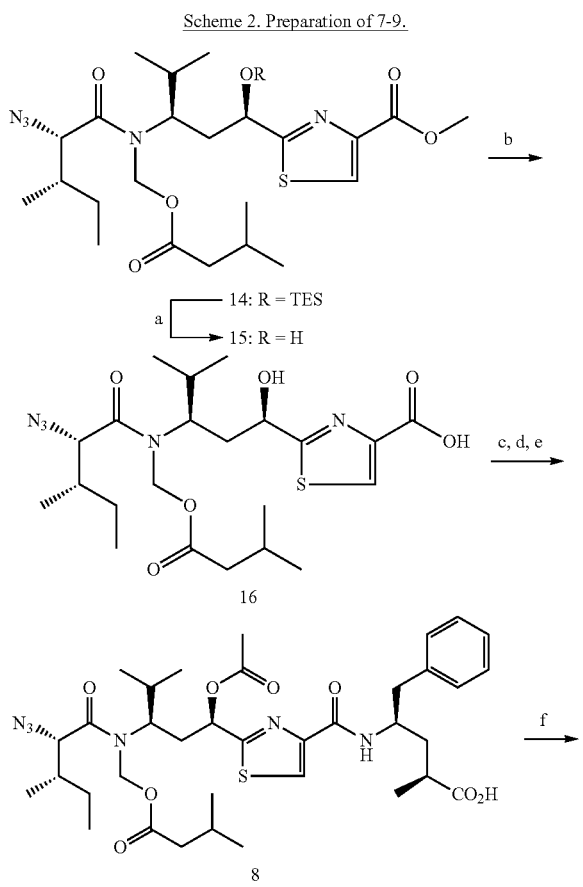

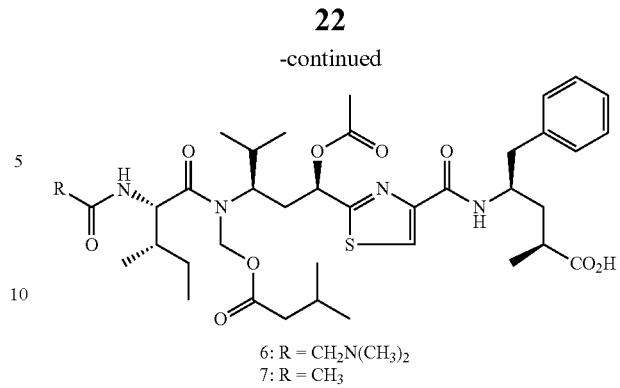

6: R = CH$_2$N(CH$_3$)$_2$
7: R = CH$_3$

Reagents and conditions: a) AcOH/THF/H$_2$O, 73%; b) Me$_3$SnOH, Cl(CH$_2$)$_2$Cl, 60° C., 36%; c) pentafluorophenol, 1,3-diisopropylcarbodiimide, CH$_2$Cl$_2$; d) 17, i-Pr$_2$EtN, DMF; e) Ac$_2$O, pyridine, then H$_2$O/dioxane, 39% yield for three steps; f) 18 or 19, H$_2$, Pd/C, EtOAc then H$_2$O/dioxane, 48% (7) or 77% (8).

Compound 10, which is directly analogous to tubulysin D with the O-acyl N,O-acetal being replaced by an N-Me amide, was synthesized starting from azide 20, which served as an early intermediate in the synthesis of tubulysin D (Scheme 3). Deprotonation of the Tuv-amide with KHMDS followed by addition of methyl iodide provided N-Me amide precursor 21. Silyl group deprotection followed by reductive coupling in the presence of the pentafluorophenyl ester of D-N-methyl pipecolinic acid (22) then provided Mep-coupled product 23. Cleavage of the methyl ester, followed by coupling with tubuphenylalanine and acetylation of the Tuv-alcohol afforded descarboxy analogue 10. Compound 11 was prepared in a similar manner to 10. Heating ester 23 in the presence of methylamine directly provided amide 25 (Scheme 3). Acetylation then afforded analogue 11.

Scheme 3. Preparation of 10 and 11.

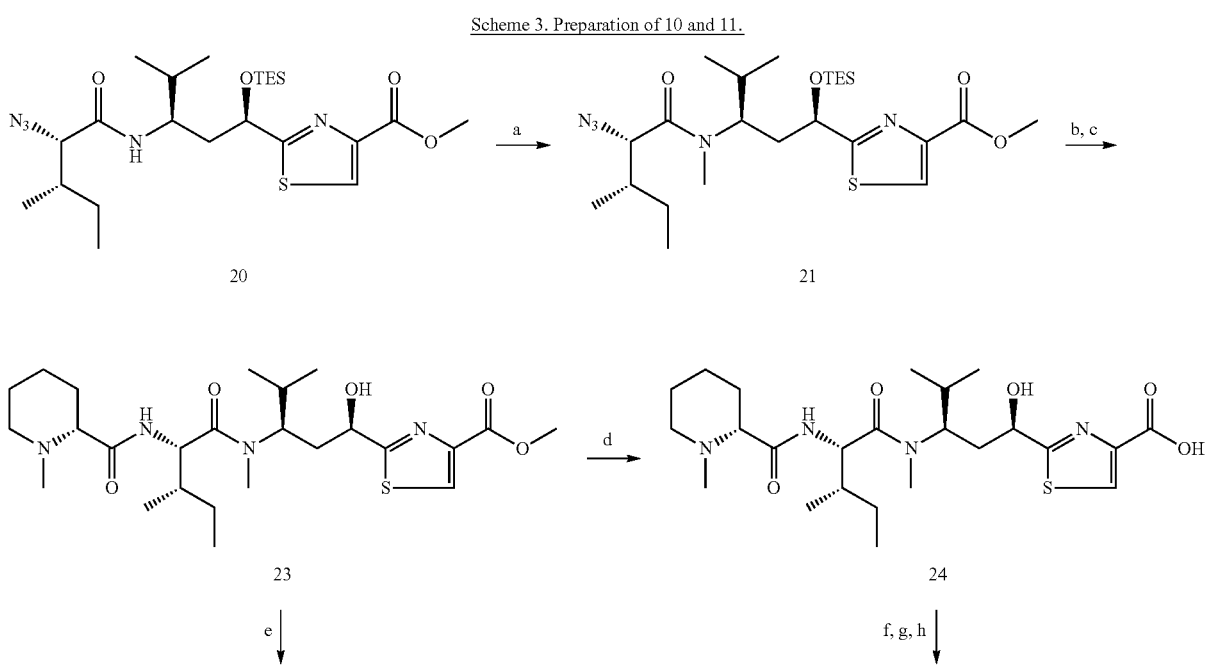

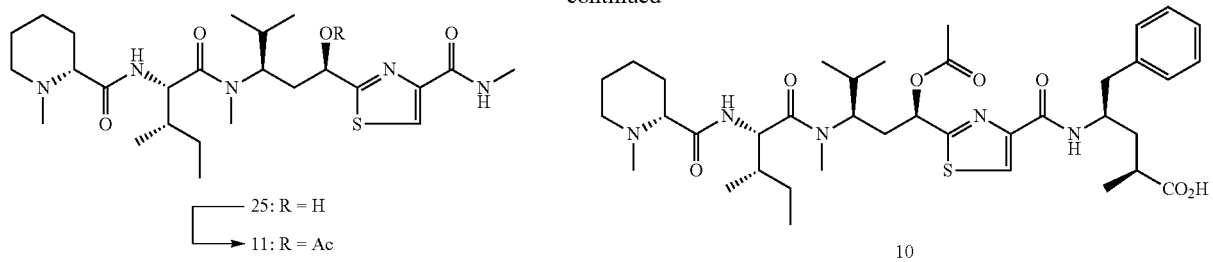

25: R = H
11: R = Ac

10

Reagents and conditions: a) potassium bis(trimethylsilyl)amide, THF, -45° C. then methyl iodide, 82%; b) 22, H$_2$, Pd/C, EtOAc; c) AcOH/THF/H$_2$O, 87% for two steps; d) Me$_3$SnOH, Cl(CH$_2$)$_2$Cl, 60° C., 88%; e) methylamine, THF/MeOH, 100° C., 52%; f) PFP, DIC, CH$_2$Cl$_2$; g) 17, i-Pr$_2$EtN, DMF; h) Ac$_2$O, pyridine, then H$_2$O/dioxane, 56% for three steps; i) Ac$_2$O, pyridine, 72%.

An exemplary synthesis of N-methyl tubulysin analogue according to Formula IIa (40) began with the preparation of thiazole 30 in 78% yield over three steps from commercially available diethoxyacetonitrile (27), according to art-recognized methods (Scheme 4). This pathway easily gives large quantities of thiazole precursor 30. Addition of the metalloenamine derived from N-tert-butanesulfinyl ketimine 26 to thiazole aldehyde 30 then provided β-hydroxy imine 31 (Scheme 5). Excess LDA (3.5 equiv) and ClTi(O-i-Pr)$_3$ (3 equiv) were both necessary to achieve high conversion and diastereoselectivity (93:7). Stereoselective reduction of imine 31 was accomplished with 92:8 dr using NaBH$_4$ and Ti(OEt)$_4$. The reaction was performed at low temperatures to prevent reduction of the ethyl ester and to increase selectivity. After chromatography, N-tert-butanesulfinyl tubuvaline ethyl ester (32) was isolated in diastereomerically pure form in 74% yield over the two steps.

Scheme 4. Synthesis of thiazole aldehyde 30

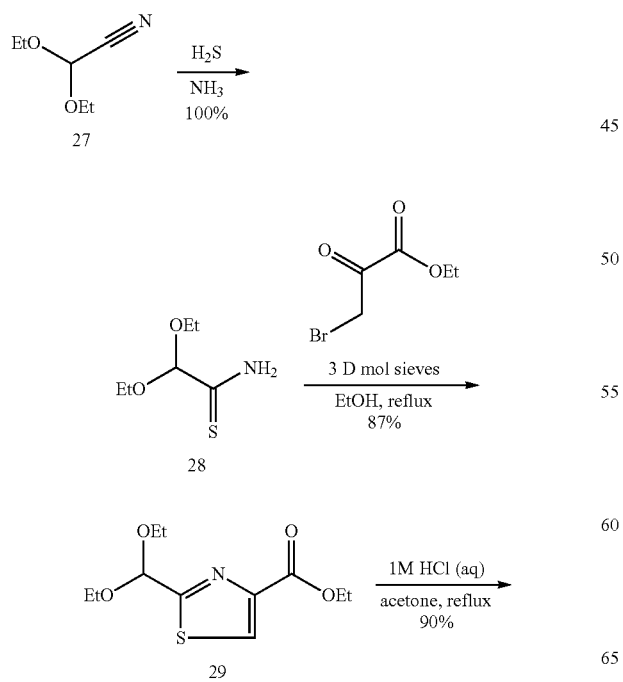

-continued

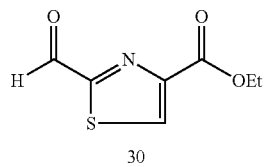

30

Scheme 5. Stereoselective synthesis of N-tert-butanesulfinyl tubuvaline ethyl ester (32)

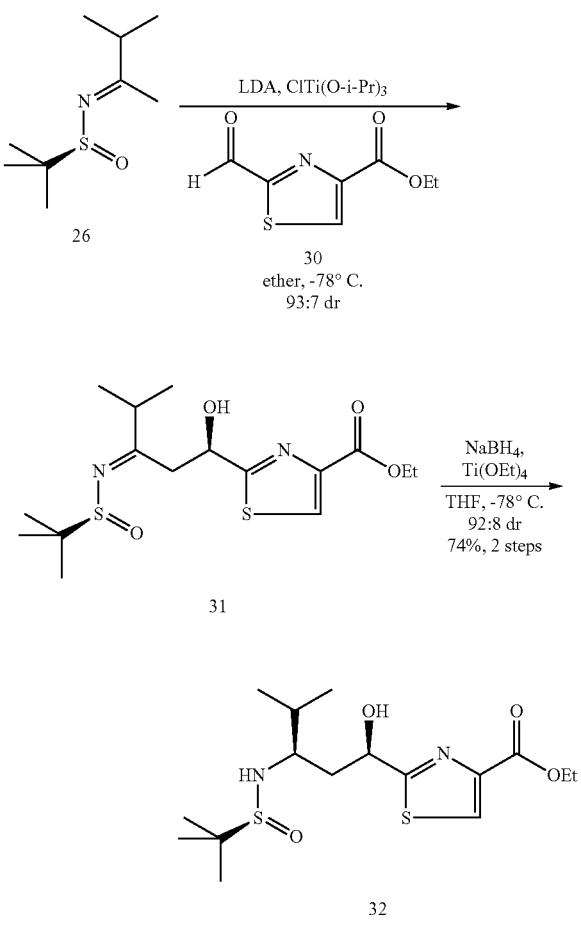

Scheme 6. Outline of 1,3-tetrahydrooxazine formation and reduction from N-sulfinyl-1,3-amino alcohol 32

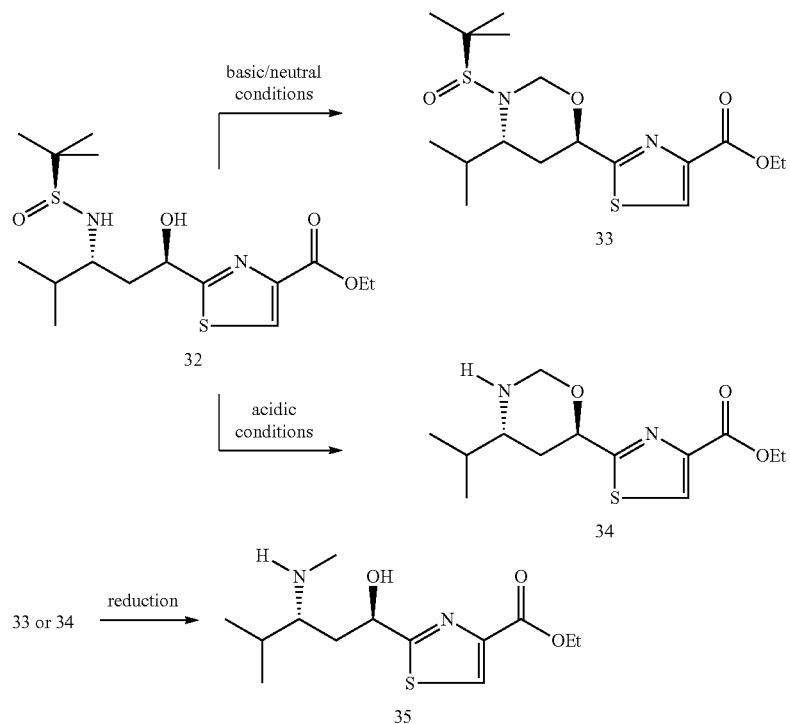

The direct alkylation of N-sulfinyl-1,3-amino alcohol 32 under basic conditions was first attempted using dihalogenated methylene reagents such as $CH_2Br_2$. Condensation of 32 with paraformaldehyde, 1 equiv of TsOH in benzene with heating at 70° C. resulted in complete conversion to sulfinyl-deprotected tetrahydrooxazine 34 in less than 2 h. Unfortunately, 34 was prohibitively unstable and hydrolyzed upon purification via silica gel or reverse-phase chromatography. Attempts to convert the crude product mixture directly to the desired N-methyl tubuvaline 35 via reduction with $NaCNBH_3$ gave instead the undesired dimethylated product due to contaminating amounts of paraformaldehyde that remained after workup. Therefore, focus turned to the preparation of tetrahydrooxazine 33, which was more stable and isolable. Condensation of 32 with paraformaldehyde, with no added acid, in toluene with heating at 70° C. resulted in complete conversion to sulfinyl-protected tetrahydrooxazine 33.

When the reaction was performed on a preparative scale, 33 proved to be stable to silica gel chromatography and was obtained in 87% yield (Scheme 7). Reduction of 33 with support-bound cyanoborohydride ($MP-BH_3CN$) resin under acidic conditions then readily provided 35 in 97% yield as the free amine after silica gel chromatography in the presence of $NH_4OH$. Accordingly, N-methyl tubuvaline ethyl ester (35) was prepared in 49% yield over 7 steps, and serves as a versatile and scalable intermediate for the construction of N-methyl tubulysin analogues with variation at the Mep, Ile, or Tup/Tut positions.

Scheme 7. Synthesis of N-methyl tubuvaline ethyl ester (35)

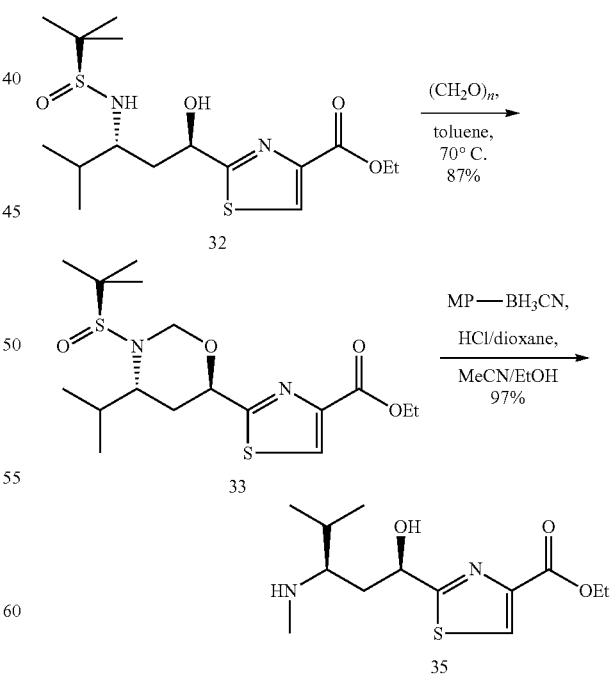

Because 36 could be prepared very cleanly without any of the bis-acylated product using PS-CCD or PyBOP, ester 36 was converted to N-methyl amide 38 (Scheme 6). Ester 36 was cleanly obtained on a preparative scale from 35 using PS-CCD and HOBt in the absence of base. After purification of 36 only by filtration and aqueous extraction, heating at 90° C. in toluene under anhydrous conditions provided the desired amide product 38 in 93% yield over the two steps.

Synthesis of a representative species of the invention in which Y is a carboxylic acid is set forth in Scheme 8.

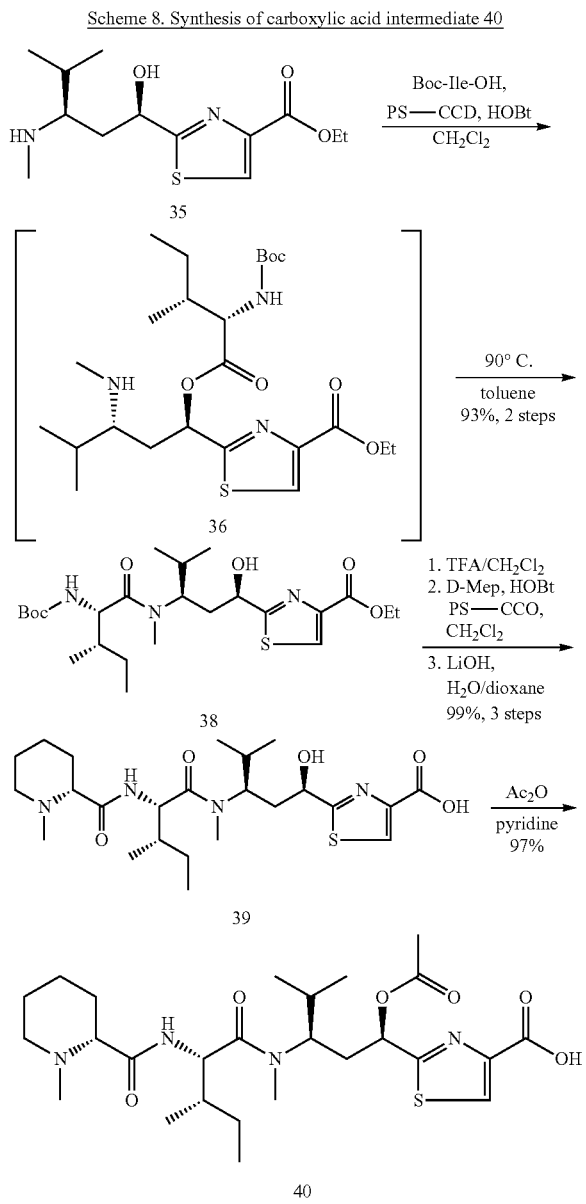

Acidic cleavage of the Boc-group of 38, followed by condensation with D-Mep and saponification of the ethyl ester with LiOH gave tripeptide 39 in 99% yield over the three steps with only a single chromatographic purification (Scheme 8). Acetylation of the free alcohol then afforded 40 in 97% yield.

A. Modifying Moieties

Exemplary modifying moieties are discussed below. The modifying groups can be selected for one or more desirable property. Exemplary properties include, but are not limited to, enhanced pharmacokinetics, enhanced pharmacodynamics, improved biodistribution, providing a polyvalent species, improved water solubility, enhanced or diminished lipophilicity, and tissue targeting.

1) Water-Soluble Polymers

The hydrophilicity of a selected species is enhanced by conjugation with polar molecules such as amine-, ester-, hydroxyl- and polyhydroxyl-containing molecules. Representative examples include, but are not limited to, polylysine, polyethyleneimine, poly(ethylene glycol) and poly(propyleneglycol). Preferred water-soluble polymers are essentially non-fluorescent, or emit such a minimal amount of fluorescence that they are inappropriate for use as a fluorescent marker in an assay.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine), wherein the polymer has about 44 or more recurring units.

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly(amino acids); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002).

The in vivo half-life, area under the curve, and/or residence time of a therapeutic agent can also be enhanced with water-soluble polymers such as polyethylene glycol (PEG) and polypropylene glycol (PPG).

Other exemplary water-soluble polymers of use in the invention include, but are not limited to linear or branched poly(alkylene oxides), poly(oxyethylated polyols), poly(olefinic alcohols), and poly(acrylomorpholine), dextran, starch, poly(amino acids), etc.

2) Water-Insoluble Polymers

The conjugates of the invention may also include one or more water-insoluble polymers. This embodiment of the invention is illustrated by the use of the conjugate as a vehicle with which to deliver a therapeutic agent in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly (isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate)polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly($\alpha$-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly(amino acids), poly(anhydrides), poly(orthoesters), poly(carbonates), poly(phosphazines), poly(phosphoesters), poly(thioesters), polysaccharides and mixtures thereof. More preferably still, the biosresorbable polymer includes a poly(hydroxy) acid component. Of the poly(hydroxy) acids, polylactic acid, polyglycolic acid, polycaproic acid, polybutyric acid, polyvaleric acid and copolymers and mixtures thereof are preferred.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly(propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. Nos. 5,410,016, which issued on Apr. 25, 1995 and 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles fabricated by different methods are of use in the present invention.

3) Biomolecules

In another preferred embodiment, the modified tubulysin analogue bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Some preferred biomolecules are essentially non-fluorescent, or emit such a minimal amount of fluorescence that they are inappropriate for use as a fluorescent marker in an assay. Other biomolecules may be fluorescent.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a reactive component on a tubulysin analogue core or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided a conjugate with biotin (or avidin or streptavidin). Thus, for example, a selectively biotinylated tubulysin analogue is elaborated by the attachment of an avidin or streptavidin moiety bearing one or more modifying groups, or vice versa.

In a further preferred embodiment, the biomolecule is selected to direct the tubulysin analogue modified by the methods of the invention to a specific intracellular compartment, thereby enhancing the delivery of the analogue to that intracellular compartment relative to the amount of underivatized analogue that is delivered to the tissue. In a still further preferred embodiment, the amount of derivatized analogue delivered to a specific intracellular compartment within a selected time period is enhanced by derivatization by at least about 20%, more preferably, at least about 40%, and more preferably still, at least about 100%. In another particularly preferred embodiment, the biomolecule is linked to the peptide by a cleavable linker that can hydrolyze once internalized. Presently, preferred biomolecules for intracellular targeting applications include transferrin, lactotransferrin (lactoferrin), melanotransferrin (p97), ceruloplasmin, divalent cation transporter and antibodies.

Site-specific and target-oriented delivery of therapeutic agents is desirable for the purpose of treating a wide variety of human diseases, such as different types of malignancies and certain neurological disorders. Such procedures are accompanied by fewer side effects and a higher efficacy of drug. Various principles have been relied on in designing these delivery systems. For a review, see Garnett, *Advanced Drug Delivery Reviews* 53:171-216 (2001).

One important consideration in designing a drug delivery system is to target tissues specifically. The discovery of tumor surface antigens has made it possible to develop therapeutic approaches where tumor cells displaying definable surface antigens are specifically targeted and killed. There are three main classes of therapeutic monoclonal antibodies (MAb) that have demonstrated effectiveness in human clinical trials in treating malignancies: (1) unconjugated MAb, which either directly induces growth inhibition and/or apoptosis, or indirectly activates host defense mechanisms to mediate antitumor cytotoxicity; (2) drug-conjugated MAb, which preferentially delivers a potent cytotoxic toxin to the tumor cells and therefore minimizes the systemic cytotoxicity commonly associated with conventional chemotherapy; and (3) radioisotope-conjugated MAb, which delivers a sterilizing dose of radiation to the tumor. See review by Reff et al., *Cancer Control* 9:152-166 (2002).

In order to arm MAbs with the power to kill malignant cells, the MAbs can be connected to a tubulysin analogue of the invention.

An immunotoxin of the invention includes a MAb, e.g., one that is mutated or chemically modified to minimized binding to normal cells conjugated to the tubulysin analogue. A large number of differentiation antigens, overexpressed receptors, or cancer-specific antigens have been identified as targets for immunotoxins, e.g., CD19, CD22, CD20, IL-2 receptor (CD25), CD33, IL-4 receptor, EGF receptor and its mutants, ErB2, Lewis carbohydrate, mesothelin, transferrin receptor, GM-CSF receptor, Ras, Bcr-Abl, and c-Kit, for the treatment of a variety of malignancies including hematopoietic cancers, glioma, and breast, colon, ovarian, bladder, and gastrointestinal cancers. See e.g., Brinkmann et al., *Expert Opin. Biol. Ther.* 1:693-702 (2001); Perentesis and Sievers, *Hematology/Oncology Clinics of North America* 15:677-701 (2001).

A number of MAbs have been used for therapeutic purposes. For example, the use of rituximab (Rituxan™), a recombinant chimeric anti-CD20 MAb, for treating certain hematopoietic malignancies was approved by the FDA in 1997. Other MAbs that have since been approved for therapeutic uses in treating human cancers include: alemtuzumab (Campath-1H™), a humanized rat antibody against CD52; and gemtuzumab ozogamicin (Mylotarg™), a calicheamicin-conjugated humanized mouse antCD33 MAb. The FDA is also currently examining the safety and efficacy of several other MAbs for the purpose of site-specific delivery of cytotoxic agents or radiation, e.g., radiolabeled Zevalin™ and Bexxar™. Reff et al., supra.

A second important consideration in designing a drug delivery system is the accessibility of a target tissue to a therapeutic agent. This is an issue of particular concern in the case of treating a disease of the central nervous system (CNS), where the blood-brain barrier prevents the diffusion of macromolecules. Several approaches have been developed to bypass the blood-brain barrier for effective delivery of therapeutic agents to the CNS.

The understanding of iron transport mechanism from plasma to brain provides a useful tool in bypassing the blood-brain barrier (BBB). Iron, transported in plasma by transferrin, is an essential component of virtually all types of cells. The brain needs iron for metabolic processes and receives iron through transferrin receptors located on brain capillary endothelial cells via receptor-mediated transcytosis and endocytosis. Moos and Morgan, *Cellular and Molecular Neurobiology* 20:77-95 (2000). Delivery systems based on transferrin-transferrin receptor interaction have been established for the efficient delivery of peptides, proteins, and liposomes into the brain. For example, peptides can be coupled with a Mab directed against the transferrin receptor to achieve greater uptake by the brain, Moos and Morgan, Supra. Similarly, when coupled with an MAb directed against the transferrin receptor, the transportation of basic fibroblast growth factor (bFGF) across the blood-brain barrier is enhanced. Song et al., *The Journal of Pharmacology and Experimental Therapeutics* 301:605-610 (2002); Wu et al., *Journal of Drug Targeting* 10:239-245 (2002). In addition, a liposomal delivery system for effective transport of the chemotherapy drug, doxorubicin, into C6 glioma has been reported, where transferrin was attached to the distal ends of liposomal PEG chains. Eavarone et al., *J. Biomed. Mater. Res.* 51:10-14 (2000). A number of US patents also relate to delivery methods bypassing the blood-brain barrier based on transferrin-transferrin receptor interaction. See e.g., U.S. Pat. Nos. 5,154,924; 5,182,107; 5,527,527; 5,833,988; 6,015,555.

There are other suitable conjugation partners for a pharmaceutical agent to bypass the blood-brain barrier. For example, U.S. Pat. Nos. 5,672,683, 5,977,307 and WO 95/02421 relate to a method of delivering a neuropharmaceutical agent across the blood-brain barrier, where the agent is administered in the form of a fusion protein with a ligand that is reactive with a brain capillary endothelial cell receptor; WO 99/00150 describes a drug delivery system in which the transportation of a drug across the blood-brain barrier is facilitated by conjugation with an MAb directed against human insulin receptor; WO 89/10134 describes a chimeric peptide, which includes a peptide capable of crossing the blood brain barrier at a relatively high rate and a hydrophilic neuropeptide incapable of transcytosis, as a means of introducing hydrophilic neuropeptides into the brain; WO 01/60411 A1 provides a pharmaceutical composition that can easily transport a pharmaceutically active ingredient into the brain. The active ingredient is bound to a hibernation-specific protein that is used as a conjugate, and administered with a thyroid hormone or a substance promoting thyroid hormone production. In addition, an alternative route of drug delivery for bypassing the blood-brain barrier has been explored. For instance, intranasal delivery of therapeutic agents without the need for conjugation has been shown to be a promising alternative delivery method (Frey, 2002, Drug Delivery Technology, 2(5):46-49).

In addition to facilitating the transportation of drugs across the blood-brain barrier, transferrin-transferrin receptor interaction is also useful for specific targeting of certain tumor cells, as many tumor cells overexpress transferrin receptor on their surface. This strategy has been used for delivering bioactive macromolecules into K562 cells via a transferrin conjugate (Wellhoner et al., *The Journal of Biological Chemistry* 266:4309-4314 (1991)), and for delivering insulin into enterocyte-like Caco-2 cells via a transferrin conjugate (Shah and Shen, *Journal of Pharmaceutical Sciences* 85:1306-1311 (1996)).

Furthermore, as more becomes known about the functions of various iron transport proteins, such as lactotransferrin receptor, melanotransferrin, ceruloplasmin, and Divalent Cation Transporter and their expression pattern, some of the proteins involved in iron transport mechanism (e.g., melanotransferrin), or their fragments, have been found to be similarly effective in assisting therapeutic agents transport across the blood-brain barrier or targeting specific tissues (WO 02/13843 A2, WO 02/13873 A2). For a review on the use of transferrin and related proteins involved in iron uptake as conjugates in drug delivery, see Li and Qian, *Medical Research Reviews* 22:225-250 (2002).

Moreover, a bone-specific delivery system has been described in which proteins are conjugated with a bone-seeking aminobisphosphate for improved delivery of proteins to mineralized tissue. Uludag and Yang, *Biotechnol. Prog.* 18:604-611 (2002). For a review on this topic, see Vyas et al., *Critical Reviews in Therapeutic Drug Carrier System* 18:1-76 (2001).

A variety of linkers may be used in the process of generating bioconjugates for the purpose of specific delivery of therapeutic agents. Suitable linkers include homo- and heterobifunctional cross-linking reagents, which may be cleavable by, e.g., acid-catalyzed dissociation, or non-cleavable (see, e.g., Srinivasachar and Neville, *Biochemistry* 28:2501-2509 (1989); Wellhoner et al., *The Journal of Biological Chemistry* 266:4309-4314 (1991)). Interaction between many known binding partners, such as biotin and avidin/streptavidin, can also be used as a means to join a therapeutic agent and a conjugate partner that ensures the specific and effective delivery of the therapeutic agent. Using the methods of the invention, proteins may be used to deliver molecules to intracellular compartments as conjugates. Proteins, peptides, hormones, cytokines, small molecules or the like that bind to specific cell surface receptors that are internalized after ligand binding may be used for intracellular targeting of conjugated therapeutic compounds. Typically, the receptor-ligand complex is internalized into intracellular vesicles that are delivered to specific cell compartments, including, but not limited to, the nucleus, mitochondria, golgi, ER, lysosome, and endosome, depending on the intracellular location targeted by the receptor. By conjugating the receptor ligand with the desired molecule, the drug will be carried with the receptor-ligand complex and be delivered to the intracellular compartments normally targeted by the receptor. The drug can therefore be delivered to a specific intracellular location in the cell where it is needed to treat a disease.

Many proteins may be used to target the tubulysin analogues to specific tissues and organs. Targeting proteins include, but are not limited to, growth factors (EPO, HGH, EGF, nerve growth factor, FGF, among others), cytokines (GM-CSF, G-CSF, the interferon family, interleukins, among others), hormones (FSH, LH, the steroid families, estrogen, corticosteroids, insulin, among others), serum proteins (albumin, lipoproteins, fetoprotein, human serum proteins, antibodies and fragments of antibodies, among others), and vitamins (folate, vitamin C, vitamin A, among others). Targeting agents are available that are specific for receptors on most cells types.

4) Therapeutic and Diagnostic Moieties

In another preferred embodiment, the tubulysin analogue is modified to include a therapeutic or diagnostic moiety. Those of skill in the art will appreciate that there is overlap between the category of therapeutic and diagnostic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities.

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

Exemplary therapeutic moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, C-1027, the duocarmycins, calicheamycin and related structures and analogues thereof.

The therapeutic moiety can also be a hormone (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progesterones, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art. An exemplary diagnostic moiety is a detectable moiety, e.g., a radioisotope or a fluorophore.

5) Probes

In yet a further embodiment, one or more of $R^1$-$R^4$ is functionalized with a detectable species, e.g., a fluorophore. Fluorescent labels have the advantage of requiring few precautions in their handling, and being amenable to high-throughput visualization techniques (optical analysis including digitization of the image for analysis in an integrated system comprising a computer). Preferred labels are typically characterized by one or more of the following: high sensitivity, high stability, low background, long lifetimes, low environmental sensitivity and high specificity in labeling.

Useful fluorophores are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful with the SLs and SPLs of the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from *Vibrio fischeri* strain (Baldwin et al., *Biochemistry* 29:5509-15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226-35 (1993)), and the like.

The compounds of the invention can be used as probes, as probes in microscopy, enzymology, clinical chemistry, molecular biology and medicine. The compounds of the invention are also useful as therapeutic agents in modalities, such as photodynamic therapy.

6) Preparation of Modified Tubulysin Analogues

Modified tubulysin analogues useful in forming the conjugates of the invention are discussed herein. In general, the tubulysin analogue and modifying group are linked together through the use of reactive groups, which are typically transformed by the linking process into a new organic functional group or unreactive species. In exemplary embodiments, the tubulysin reactive functional group(s), or a link (either a bond or a higher order linker) to a carrier molecule, is located at one or more of $R^1$-$R^4$ of Formula II. In various embodiments, the compounds of the invention include a reactive functional group, or a link (either a bond or a higher order linker) to a carrier molecule covalently attached to $R^4$ of the structure shown in Formula II. In various exemplary embodiments, the reactive functional group, or link to a carrier molecule (through a bond or higher order linker), is found at one or more substituent of Formulae II-VIII. In an exemplary embodiment, the locus for conjugation of a modifying group to the tubulysin analogue is the carboxylic acid moiety, such as is in compounds 3, 5, 6, 8, 9, 10 and 40 herein. For example, the carboxylic acid moiety can be activated (e.g., as an active ester, imidazolide, acid halide, etc.) and the activated carboxyl moiety, reacted with conjugation partner (e.g., antibodies, fluorophores, polymers (dendrimers, branched star polymers, linear polymers), chelates etc.) as described herein. The conjugation partner includes within its structure a group that reacts with the activated carboxyl moiety (e.g., an amine, alcohol, thiol, etc.). Other reactive species and reaction types, some of which are described herein, are of use to form conjugates of the tubulysin analogues.

Reactive groups and classes of reactions useful in practicing the present invention are generally those that are well known in the art of bioconjugate chemistry. Currently favored classes of reactions available with reactive tubulysin analogues are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, Smith and March, ADVANCED ORGANIC CHEMISTRY, 5th Ed., John Wiley & Sons, New York, 2001; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a tubulysin analogue nucleus or modifying group include, but are not limited to:

(a) carboxyl groups and various derivatives thereof including, but not limited to, active esters, e.g., N-hydroxysuccinimide esters, N-hydroxybenzotriazole esters, thioesters, p-nitrophenyl esters, alkyl, alkenyl, alkynyl, aromatic esters, acid halides, and acyl imidazoles;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with alkyl and acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive tubulysin core or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In another preferred embodiment, one or more of the above-recited R groups comprise a reactive group for conjugating said compound to a member selected from the group consisting of molecules and surfaces. Representative useful reactive groups are discussed in greater detail above. Additional information on useful reactive groups is known to those of skill in the art. See, for example, Hermanson, BIOCONJUGATE TECHNIQUES, Academic Press, San Diego, 1996.

In a preferred embodiment, one or more of the above-recited R groups is a linker between the tubulysin analogue core and a modifying group, such as those discussed above. A myriad of linker arm structures are feasible and of use in the present invention. In an exemplary embodiment, the linker arm (e.g., that attached to $R^4$) is a member selected from ω-carboxyl alkyl groups, ω-carboxyl substituted alkyl groups and combinations thereof. An exemplary linker group according to this structure has the formula:

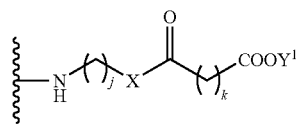

in which X is a member selected from O, S and $NR^{50}$. $R^{50}$ is preferably a member selected from H, alkyl and substituted alkyl. $Y^1$ is preferably a member selected from H and a single negative charge; and j and k are preferably members independently selected from the group consisting of integers from 1 to 18.

In another exemplary embodiment, one or more of the above-recited R groups is:

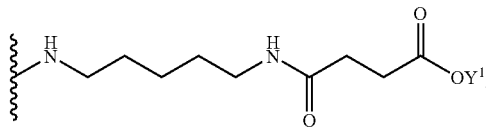

In yet another preferred embodiment, one or more of the R groups can combine characteristics of one or more of the above-recited groups. For example, one preferred R group combines both the attributes of a polyether and a reactive group:

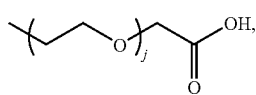

in which j is an integer between 1 and 100, inclusive. Other such "chimeric" R groups include, but are not limited to, moieties such as sugars (e.g., polyol with reactive hydroxyl), amino acids, amino alcohols, carboxy alcohols, amino thiols, and the like.

Pharmaceutical Formulations

While compounds of the present invention can be administered as the raw chemical, it is preferable to present them as a pharmaceutical composition. According to a further aspect, the present invention provides a pharmaceutical composition comprising a compound of Formula (II) or a pharmaceutically acceptable salt, hydrate or solvate thereof, together with one or more pharmaceutical carrier and optionally one or more other therapeutic ingredients. The carrier(s) are "acceptable" in the sense of being compatible with the other ingredients of the formulation and not deleterious to the recipient thereof. The term "pharmaceutically acceptable carrier" includes vehicles, diluents, excipients and other elements appropriate for incorporation into a pharmaceutical formulation.

The formulations include those suitable for oral, parenteral (including subcutaneous, intradermal, intramuscular, intravenous and intraarticular), rectal and topical (including dermal, buccal, sublingual and intraocular) administration, as well as those for administration by inhalation. The most suitable route may depend upon the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: The Science and Practice of Pharmacy, A. R. Gennaro, ed. (1995), the entire disclosure of which is incorporated herein by reference.

Pharmaceutical compositions containing compounds of Formula (II) may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient.

In general, the total daily dose ranges from about 0.1 mg per day to about 7000 mg per day, preferably about 1 mg per day to about 100 mg per day, and more preferably, about 25 mg per day to about 50 mg per day, in single or divided doses. In some embodiments, the total daily dose may range from about 50 mg to about 500 mg per day, and preferably, about 100 mg to about 500 mg per day.

Different therapeutically effective amounts may be applicable for different proliferative disorders, as will be readily known by those of ordinary skill in the art. Similarly, amounts sufficient to prevent, manage, treat or ameliorate such proliferative disorder, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate a cell proliferative disorder or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a proliferative disorder or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

It is further recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

It should be understood that in addition to the ingredients particularly mentioned above, the formulations of this invention may include other agents conventional in the art having regard to the type of formulation in question, for example those suitable for oral administration may include flavoring agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compressing or molding the compound of Formula (I), optionally using one or more additional ingredient. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: The Science and Practice of Pharmacy, pages 1660-1675 (1995).

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The pharmaceutically acceptable carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Exemplary formulations, are well known to those skilled in the art, and general methods for preparing them are found in any standard pharmacy school textbook, for example, Remington, THE SCIENCE AND PRACTICE OF PHARMACY, 21st Ed., Lippincott.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The Methods

The invention provides compositions and methods of use in treating, preventing or ameliorating one or more proliferative disorder. The method includes administering to a subject in need of treating, preventing or ameliorating a proliferative disorder a therapeutically useful amount of a compound or composition of the invention.

As used herein, the terms "proliferative disorder", "hyperproliferative disorder," and "cell proliferation disorder" are used interchangeably to mean a disease or medical condition involving pathological growth of cells. Such disorders include cancer, and non-cancerous proliferative disorders.

The term "treating" when used in connection with the foregoing disorders means amelioration, prevention (prophylaxis) or relief from the symptoms and/or effects associated with these disorders and includes the prophylactic administration of a compound of the invention, or a pharmaceutically acceptable salt, hydrate, solvate, prodrug, metabolite, etc., to substantially diminish the occurrence or seriousness of the condition. Administration of a "therapeutically effective dose" to a subject is a preferred method of "treating" a disorder.

The magnitude of a therapeutically effective dose of a compound of the invention will vary with the nature and severity of the condition to be treated and the route of administration. The dose, and perhaps the dose frequency, will also vary according to the age, body weight and response of the individual patient. In general, the total daily dose ranges of compounds of the present invention will be from about 25 mg per day to about 1000 mg per day, preferably about 100 mg per day to about 600 mg per day, in single or divided doses.

Any suitable route of administration may be employed. For example, oral, rectal, intranasal, and parenteral (including subcutaneous, intramuscular, and intravenous) routes may be employed. Dosage forms can include tablets, troches, dispersions, suspensions, solutions, capsules and patches.

Cancers that can be treated or prevented by the compositions and methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1(murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of The Chemotherapy Sourcebook, Michael C. Perry Ed., Williams & Williams (1992) and Section 36 of Holland Frie Cancer Medicine 5th Ed., Bast et al. Eds., B. C. Decker Inc. (2000). The entire teachings of the preceding references are incorporated herein by reference.

In one embodiment, the disclosed method is believed to be particularly effective in treating subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1(acute) cell line); and lymphoma (e.g., as exemplified by the U937 cell line).

Some of the disclosed methods can be particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

When used to treat a non-cancerous proliferative disorder, the tubulysin analogues and conjugates described herein can be administered as a monotherapy. Alternatively, the compound can be administered in combination with one or more additional agents that inhibits cell proliferation or provide other desirable benefits, for example, anticancer agents, immunosuppressants, and the like. Specific examples of suitable agents for use in combination with the compounds of this invention include members of the taxane family, rapamycin, rapamycin analogs, and the like.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

The following examples are provided to illustrate selected embodiments of the invention and are not to be construed as limiting its scope.

EXAMPLES

General Methods

Compounds 9, 12, 14, 17, 20, and 22 were prepared as previously described. Peltier et al., *J. Am. Chem. Soc.* 2006, 128, 16018-16019. Unless otherwise noted, all starting materials were obtained from commercial suppliers and used without further purification. Methyl iodide was filtered through a plug of basic alumina (Brockman activity 1) immediately prior to use. Toluene, THF, ether, dioxane, and $CH_2Cl_2$ were dried over alumina under a nitrogen atmosphere. Methanol, i-$Pr_2NH$, i-$Pr_2EtN$, dichloroethane, and pyridine were distilled from $CaH_2$ immediately prior to use. Where noted, water and acetic acid were degassed using three consecutive freeze pump thaw cycles. Reactions were carried out in flame or oven-dried glassware under a $N_2$ atmosphere. Extracts were dried over $Na_2SO_4$. Products were concentrated using a Büchi rotary evaporator under reduced pressure. Chromatography was carried out either with Merck 60 Å 230-400 mesh silica gel or via HPFC purification on a Biotage SP1 instrument (Charlottesville, Va.) equipped with a normal-phase Biotage Si flash column or reverse-phase Biotage C18 column. Where noted, water was removed from samples by lyophilization using a Labconco Corp. freeze-dry system (Kansas City, Mo.). Optical rotation measurements were performed on a Perkin-Elmer 241 polarimeter. Optical rotations ([α]) are measured in deg $cm^3$ $g^{-1}$ $dm^{-1}$. Concentration (c) is measured in g $dL^{-1}$. IR spectra were recorded on a Nicolet Avatar 360 FTIR spectrometer equipped with an attenuated total reflectance accessory and only partial data are listed. $^1H$ NMR and $^{13}C$ NMR spectra were obtained at room temperature with Bruker AV-400 and DRX-500 spectrometers. Chemical shifts are expressed in ppm relative to internal solvent. High-resolution mass spectra were performed by the University of California at Berkeley Micro-Mass Facility.

Example 1

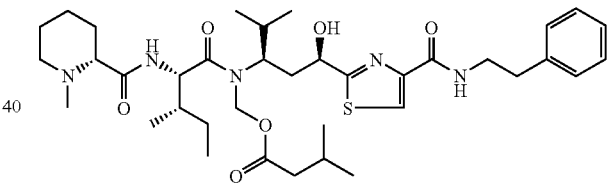

Acid 12 (40.0 mg, 0.0670 mmol) was added to a solution of pentafluorophenol (19.0 mg, 0.101 mmol) and 1,3-diisopropylcarbodiimide (11.5 μL, 0.0737 mmol) in 0.51 mL $CH_2Cl_2$ at 0° C. The reaction mixture was warmed to rt, stirred for 24 h, and concentrated. EtOAc (10 mL) was added, and the crude product was filtered, with rinsing of the reaction vessel with EtOAc. The filtrate was concentrated, and the crude material was used without further purification. DMF (0.270 mL, 0.25 M) was added to the crude product at 0° C., followed by phenethylamine (10.2 μL, 0.0804 mmol) and i-$Pr_2EtN$ (23.0 μL, 0.134 mmol). The reaction mixture was allowed to warm to rt, stirred for 24 h, and concentrated. Normal-phase HPFC purification (100:0 to 90:10 $CH_2Cl_2$:MeOH) afforded 23.0 mg (49%) of 13a. $[α]_D^{23}$=+15.0 (c=1.5, MeOH). IR: 1497, 1544, 1661, 1738, 2793, 2874, 2934, 2961, 3301, 3370 $cm^{-1}$.
$^1H$ NMR (500 MHz, MeOD): δ 0.80-0.92 (m, 12H), 0.97 (d, 3H, J=6.9 Hz), 1.00 (d, 3H, J=6.7 Hz), 1.19-1.30 (m, 3H), 1.49-1.65 (m, 5H), 1.69-1.75 (m, 2H), 1.98-2.18 (m, 7H), 2.14 (s, 3H), 2.58 (app d, 1H, J=10.4 Hz), 2.91 (m, 1H), 2.92 (app t, 2H, J=7.5 Hz), 3.55-3.66 (m, 2H), 4.58 (d, 1H, J=9.8 Hz), 4.75 (d, 1H, J=10.2 Hz), 5.51 (d, 1H, J=12.2 Hz), 6.17 (d, 1H, J=12.2 Hz), 7.18-7.21 (m, 1H), 7.24-7.30 (m, 4H), 8.09 (s, 1H). $^{13}C$ NMR (125 MHz, MeOD): δ 10.7, 16.2, 20.7, 22.77, 22.81, 24.3, 25.96, 25.97, 26.1, 26.7, 31.5, 36.71, 36.73, 37.6, 38.8, 42.0, 44.4, 44.7, 55.4, 56.6, 69.5, 70.3, 124.7, 127.5, 129.6, 129.8, 140.3, 150.7, 163.5, 173.4, 175.5, 178.2, 179.1. HRMS (FAB) calcd for $C_{37}H_{58}N_5O_6S$ (M+H): 700.4108. Found: 700.4105.

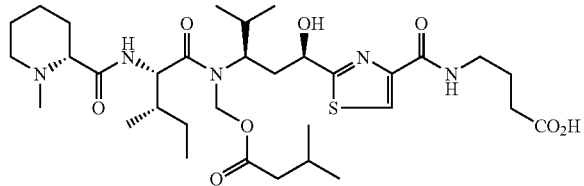 [SMILES: CC[C@H](C)[C@H](NC(=O)[C@H]1CCCCN1C)C(=O)N(COC(=O)CC(C)C)[C@H](C[C@@H](O)c1nc(C(=O)NCCCC(=O)O)cs1)C(C)C]

1.2 Synthesis of 3-methyl-butyric acid ((1-{2-[4-(3-carboxy-propylcarbamoyl)-thiazol-2-yl]-2-hydroxy-ethyl}-2-methyl-propyl)-{3-methyl-2-[(1-methyl-piperidine-2-carbonyl)-amino]-pentanoyl}-amino)-methyl ester (13b)

Acid 12 (25.0 mg, 0.0419 mmol) was added to a solution of pentafluorophenol (12.0 mg, 0.0628 mmol) and 1,3-diisopropylcarbodiimide (7.22 μL, 0.0461 mmol) in 0.31 mL of $CH_2Cl_2$ at 0° C. The reaction mixture was warmed to rt, stirred for 24 h, and concentrated. EtOAc (10 mL) was added, and the crude product was filtered, with rinsing of the reaction vessel with EtOAc. The filtrate was concentrated and the crude material was used without further purification. DMF (0.170 mL, 0.25 M) was added to the crude product at 0° C., followed by the 4-aminobutyric acid (5.18 mg, 0.0503 mmol) and i-$Pr_2EtN$ (18.2 μL, 0.105 mmol). The reaction mixture was allowed to warm to rt, stirred for 24 h, and concentrated. Normal-phase HPFC purification (100:0 to 90:10 $CH_2Cl_2$:MeOH) afforded 20.0 mg (70%) of 13b. $[α]_D^{23}=+10.3$ (c=1.0, MeOH). IR: 1451, 1550, 1643, 1658, 1736, 2795, 2872, 2925, 2961, 3365 cm$^{-1}$. $^1$H NMR (500 MHz, MeOD): δ 0.81-0.85 (m, 3H), 0.88-0.91 (m, 9H), 0.97 (d, 3H, J=7.0 Hz), 1.00 (d, 3H, J=6.1 Hz), 1.19-1.26 (m, 1H), 1.27-1.34 (m, 1H), 1.53-1.66 (m, 5H), 1.70-1.77 (m, 2H), 1.91 (m, 3H), 1.99-2.06 (m, 4H), 2.13-2.19 (m, 3H), 2.19 (s, 3H), 2.28 (app t, 2H, J=7.3 Hz), 2.70 (app d, 1H, J=11.4 Hz), 2.96 (app d, 1H, J=11.1 Hz), 3.42 (app t, 2H, J=7.2 Hz), 4.59 (d, 1H, J=9.2 Hz), 4.76 (d, 1H, J=9.0 Hz), 5.51 (d, 1H, J=11.9 Hz), 6.16 (d, 1H, J=12.2 Hz), 8.08 (s, 1H). $^{13}$C NMR (125 MHz, MeOD): δ 10.7, 16.2, 20.7, 22.77, 22.81, 24.1, 25.9, 26.7, 27.3, 31.4, 35.6, 37.6, 38.89, 38.90, 40.4, 43.0, 44.44, 44.48, 55.4, 56.6, 58.7, 69.9, 70.1, 124.5, 150.9, 163.6, 173.4, 174.92, 174.95, 174.96, 180.9. HRMS (FAB) calcd for $C_{33}H_{56}N_5O_8S$ (M+H): 682.3850. Found: 682.3861.

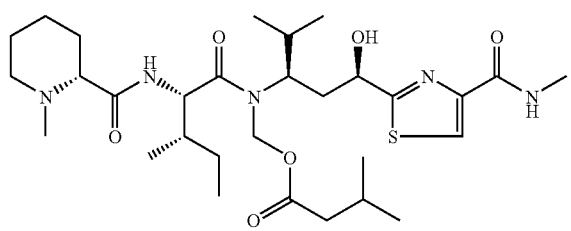 [SMILES: CC[C@H](C)[C@H](NC(=O)[C@H]1CCCCN1C)C(=O)N(COC(=O)CC(C)C)[C@H](C[C@@H](O)c1nc(C(=O)NC)cs1)C(C)C]

1.3 Synthesis of 3-methyl-butyric acid ({1-[2-hydroxy-2-(4-methylcarbamoyl-thiazol-2-yl)-ethyl]-2-methyl-propyl}-{3-methyl-2-[(1-methyl-piperidine-2-carbonyl)-amino]-pentanoyl}-amino)-methyl ester (13c)

Acid 12 (30.0 mg, 0.0503 mmol) was added to a solution of pentafluorophenol (14.0 mg, 0.0754 mmol) and 1,3-diisopropylcarbodiimide (8.70 μL, 0.0553 mmol) in 0.38 mL of $CH_2Cl_2$ at 0° C. The reaction mixture was warmed to rt, stirred for 24 h, and concentrated. EtOAc (10 mL) was added, and the crude product was filtered, with rinsing of the reaction vessel with EtOAc. The filtrate was concentrated, and the crude material was used without further purification. DMF (0.201 mL, 0.25 M) was added to the crude product at 0° C., followed by the hydrochloride salt of methylamine (18.0 mg, 0.151 mmol) and i-$Pr_2EtN$ (44.0 μL, 0.251 mmol). The reaction mixture was allowed to warm to rt, stirred for 24 h at rt, and concentrated. Normal-phase HPFC purification (100:0 to 90:10 $CH_2Cl_2$:MeOH) afforded 31.0 mg (68%) of 13c. $[α]_D^{23}=+15.5$ (c=1.0, MeOH). IR: 1420, 1498, 1654, 1737, 2791, 2872, 2934, 2961, 3322, 3367 cm$^{-1}$. $^1$H NMR (500 MHz, MeOD): δ 0.83 (d, 3H, J=5.9 Hz), 0.90 (app t, 9H, J=7.5 Hz), 0.98 (app t, 6H, J=7.5 Hz), 1.20-1.30 (m, 3H), 1.49-1.63 (m, 5H), 1.69-1.72 (m, 2H), 1.98-2.06 (m, 5H), 2.13 (s, 3H), 2.14-2.17 (m, 2H), 2.55 (app d, 1H, J=11.5 Hz), 2.88-2.91 (m, 1H), 2.93 (s, 3H), 4.59 (d, 1H, J=9.9 Hz), 4.75 (d, 1H, J=10.8 Hz), 5.51 (d, 1H, J=12.1 Hz), 6.18 (d, 1H, J=12.1 Hz), 8.08 (s, 1H). $^{13}$C NMR (125 MHz, MeOD): δ 10.6, 16.2, 20.7, 22.7, 22.8, 24.3, 25.9, 26.1, 26.3, 26.6, 31.56, 31.64, 36.9, 37.6, 38.8, 44.4, 44.7, 55.3, 56.6, 69.5, 70.4, 124.4, 150.7, 164.2, 164.9, 173.4, 175.7, 179.1. HRMS (FAB) calcd for $C_{30}H_{52}N_5O_6S$ (M+H): 610.3638. Found: 610.3634.

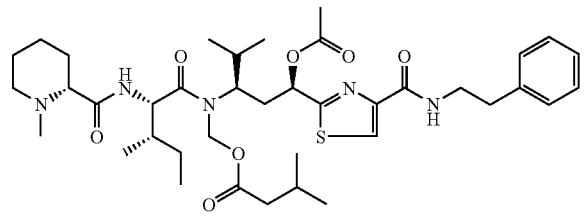 [SMILES: CC[C@H](C)[C@H](NC(=O)[C@H]1CCCCN1C)C(=O)N(COC(=O)CC(C)C)[C@H](C[C@@H](OC(C)=O)c1nc(C(=O)NCCc2ccccc2)cs1)C(C)C]

1.4 Synthesis of 3-methyl-butyric acid ({1-[2-acetoxy-2-(4-phenethylcarbamoyl-thiazol-2-yl)-ethyl]-2-methyl-propyl}-{3-methyl-2-[(1-methyl-piperidine-2-carbonyl)-amino]-pentanoyl}-amino)-methyl ester (2)

A 0.10 M solution of 13a (15.5 mg, 0.0221 mmol) in pyridine (0.221 mL) was cooled to 0° C., and acetic anhydride (10.0 μL, 0.111 mmol) was added. The reaction mixture was allowed to warm to rt over 2 h and was stirred at rt for 24 h. The solvent was removed under reduced pressure. Column chromatography (100:0 to 90:10 $CH_2Cl_2$:MeOH) afforded 16.4 mg (99%) of 2 as an amorphous solid. $[α]_D^{23}=+50.0$ (c=0.4, MeOH). IR: 1229, 1370, 1426, 1455, 1497, 1544, 1667, 1742, 2848, 2874, 2934, 2961, 3306, 3383 cm$^{-1}$. $^1$H NMR (500 MHz, MeOD): δ 0.79 (d, 3H, J=6.3 Hz), 0.83 (d, 3H, J=6.5 Hz), 0.86 (d, 3H, J=6.6 Hz), 0.90 (app t, 3H, J=7.3

Hz), 0.96 (d, 3H, J=7.17 Hz), 1.05 (d, 3H, J=6.4 Hz), 1.16-1.22 (m, 1H), 1.28-1.36 (m, 2H), 1.53-1.68 (m, 4H), 1.75-1.86 (m, 3H), 1.91-2.08 (m, 3H), 2.10-2.14 (m, 1H), 2.13 (s, 3H), 2.17-2.26 (m, 1H), 2.24 (s, 3H), 2.48 (app t, 1H, J=13.1 Hz), 2.72 (app t, 1H, J=10.8 Hz), 2.91 (app t, 2H, J=7.5 Hz), 2.99 (app d, 1H, J=11.7 Hz), 3.62 (m, 2H), 4.43 (br s, 1H), 4.60 (d, 1H, J=9.3 Hz), 5.40 (d, 1H, J=12.7 Hz), 5.85 (d, 1H, J=11.3 Hz), 6.16 (d, 1H, J=12.5 Hz), 7.18-7.21 (m, 1H), 7.25-7.30 (m, 4H), 8.17 (s, 1H). $^{13}$C NMR (125 MHz, MeOD) δ 10.7, 16.4, 20.3, 20.7, 20.8, 22.71, 22.73, 24.0, 25.6, 25.8, 26.7, 31.4, 32.2, 35.7, 36.7, 37.3, 42.0, 44.2, 44.4, 55.1, 56.5, 70.0, 70.6, 125.7, 127.5, 129.6, 129.9, 140.3, 150.7, 163.1, 170.6, 171.9, 173.2, 174.6, 176.5. HRMS (FAB) calcd for $C_{39}H_{60}N_5O_7S$ (M+H): 742.4213. Found: 742.4206.

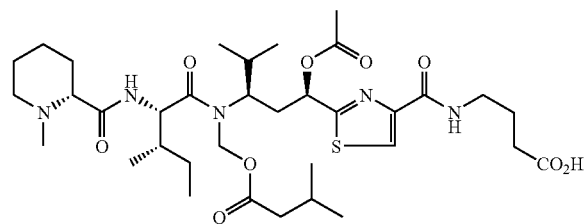 [SMILES: CC[C@H](C)[C@H](NC(=O)[C@H]1CCCCN1C)C(=O)N(COC(=O)CC(C)C)[C@H](C[C@@H](OC(C)=O)c1nc(C(=O)NCCCC(=O)O)cs1)C(C)C]

1.5 Synthesis of 3-Methyl-butyric acid ((1-{2-acetoxy-2-[4-(3-carboxy-propylcarbamoyl)-thiazol-2-yl]-ethyl}-2-methyl-propyl)-{3-methyl-2-[(1-methyl-piperidine-2-carbonyl)-amino]-pentanoyl}-amino)-methyl ester (3)

A 0.10 M solution of 13b (15.0 mg, 0.0220 mmol) in pyridine (0.220 mL) was cooled to 0° C., and acetic anhydride (10.4 µL, 0.110 mmol) was added. The reaction mixture was allowed to warm to rt over 2 h and was stirred at rt for 24 h. The reaction mixture was then cooled to 0° C., and a 1:1 mixture of dioxane/water (0.630 mL) was added. The mixture was allowed to warm to rt and was stirred for 12 h at rt. The solvent was removed under reduced pressure. Column chromatography (100:0 to 90:10 $CH_2Cl_2$:MeOH) afforded 13.0 mg (81%) of 3 as an amorphous solid. $[α]_D^{23}$=+24.3 (c=0.7, MeOH). IR: 1371, 1420, 1497, 1544, 1667, 1741, 2342, 2360, 2840, 2872, 2929, 2961, 3293, 3368 cm$^{-1}$. $^1$H NMR (500 MHz, MeOD): δ 0.79 (d, 3H, J=6.7 Hz), 0.85 (d, 3H, J=6.9 Hz), 0.87-0.92 (m, 6H), 0.96 (d, 3H, J=6.6 Hz), 1.05 (d, 3H, J=6.3 Hz), 1.15-1.23 (m, 1H), 1.35-1.42 (m, 1H), 1.57-1.65 (m, 3H), 1.69-1.72 (m, 1H), 1.77-1.81 (m, 1H), 1.84-1.93 (m, 4H), 1.95-2.01 (m, 2H), 2.08-2.18 (m, 2H), 2.13 (s, 3H), 2.28-2.39 (m, 4H), 2.33 (s, 3H), 2.48-2.53 (m, 1H), 2.94 (app d, 1H, J=10.1 Hz), 3.08 (app d, 1H, J=11.3 Hz), 3.40-3.43 (m, 2H), 4.41 (br s, 1H), 4.60 (d, 1H, J=9.5 Hz), 5.40 (d, 1H, J=12.4 Hz), 5.87 (d, 1H, J=10.8 Hz), 6.13 (d, 1H, J=10.8 Hz), 8.18 (s, 1H). $^{13}$C NMR (125 MHz, MeOD) δ 10.7, 16.4, 20.3, 20.70, 20.76, 22.73, 22.74, 23.7, 25.54, 22.56, 26.7, 26.9, 31.1, 32.2, 34.7, 35.9, 37.4, 40.2, 44.18, 44.25, 55.2, 56.5, 69.7, 70.7, 125.6, 150.8, 163.2, 170.7, 171.9, 173.3, 173.8, 176.4, 180.5. HRMS (FAB) calcd for $C_{35}H_{58}N_5O_9S$ (M+H): 724.3955. Found: 724.3937.

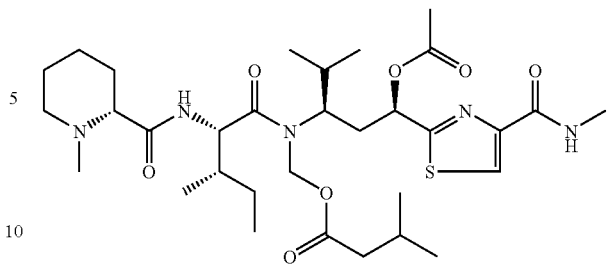

1.6 Synthesis of 3-methyl-butyric acid ({1-[2-acetoxy-2-(4-methylcarbamoyl-thiazol-2-yl)-ethyl]-2-methyl-propyl}-{3-methyl-2-[(1-methyl-piperidine-2-carbonyl)-amino]-pentanoyl}-amino)-methyl ester (4)

A 0.10 M solution of 13c (10.5 mg, 0.0172 mmol) in pyridine (0.172 mL) was cooled to 0° C., and acetic anhydride (8.10 µL, 0.0861 mmol) was added. The reaction mixture was allowed to warm to rt over 2 h and was stirred at rt for 24 h. The solvent was removed under reduced pressure. Column chromatography (100:0 to 90:10 $CH_2Cl_2$:MeOH) afforded 10.1 mg (90%) of 4 as an amorphous solid. $[α]_D^{23}$=+60.5 (c=0.6, MeOH). IR: 1229, 1371, 1420, 1466, 1499, 1549, 1665, 1742, 2792, 2848, 2875, 2934, 2961, 3305, 3380 cm$^{-1}$. $^1$H NMR (500 MHz, MeOD): δ 0.78 (d, 3H, J=7.0 Hz), 0.84 (d, 3H, J=6.7 Hz), 0.87-0.91 (m, 6H), 0.96 (d, 3H, J=6.7 Hz), 1.04 (d, 3H, J=6.3 Hz), 1.25-1.15 (m, 1H), 1.24-132 (m, 1H), 1.48-1.65 (m, 4H), 1.72-1.75 (m, 2H), 1.79-1.86 (m, 1H), 1.93-2.18 (m, 5H), 2.13 (s, 3H), 2.15 (s, 3H), 2.22-2.29 (m, 1H), 2.47-2.57 (m, 2H), 2.89-2.94 (m, 1H), 2.92 (s, 3H), 4.43 (br s, 1H), 4.60 (d, 1H, J=10.1 Hz), 5.39 (d, 1H, J=12.2 Hz), 5.87 (d, 1H, J=12.0 Hz), 6.18 (d, 1H, J=12.5 Hz), 8.16 (s, 1H). $^{13}$C NMR (125 MHz, MeOD) δ 10.7, 16.4, 20.3, 20.69, 20.74, 22.68, 22.69, 24.3, 25.6, 26.1, 26.3, 26.6, 31.5, 32.2, 35.9, 37.3, 44.2, 44.7, 55.0, 56.6, 70.4, 70.7, 125.5, 150.7, 163.8, 170.8, 171.9, 173.3, 175.5, 176.7. HRMS (FAB) calcd for $C_{32}H_{54}N_5O_7S$ (M+H): 652.3744. Found: 652.3719.

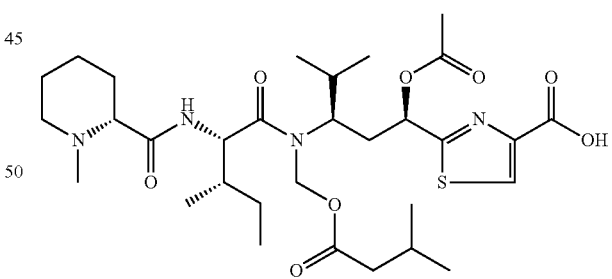

1.7 Synthesis of 2-[1-acetoxy-4-methyl-3-((3-methyl-butyryloxymethyl)-{3-methyl-2-[(1-methyl-piperidine-2-carbonyl)-amino]-pentanoyl}-amino)-pentyl]-thiazole-4-carboxylic acid (5)

A 0.10 M solution of 12 (25.0 mg, 0.0419 mmol) in pyridine (0.420 mL) was cooled to 0° C., and acetic anhydride (19.8 µL, 0.209 mmol) was added. The reaction mixture was allowed to warm to rt over 2 h and was stirred at rt for 24 h. The reaction mixture was then cooled to 0° C., and a 1:1 mixture of dioxane/water (1.50 mL) was added. The mixture was allowed to warm to rt and was stirred for 12 h at rt. The solvent was removed under reduced pressure. Column chromatography (100:0 to 90:10 $CH_2Cl_2$:MeOH) afforded 26.0 mg (97%) of 5 as an amorphous solid. $[\alpha]_D^{23}$=+12.0 (c=2.6, MeOH). IR: 1371, 1422, 1471, 1499, 1597, 1666, 1743, 2874, 2934, 2962, 3384 cm$^{-1}$. $^1$H NMR (500 MHz, MeOD): δ 0.82-0.84 (m, 3H), 0.88-0.92 (m, 9H), 0.96 (d, 3H, J=6.7 Hz), 1.01 (d, 3H, J=6.3 Hz), 1.15-1.22 (m 1H), 1.52-1.70 (m, 4H), 1.75-1.82 (m, 2H), 1.93-2.05 (m, 4H), 2.12 (s, 3H), 2.20-2.23 (m, 4H), 2.39-2.55 (m, 6H), 3.15-3.22 (m, 1H), 4.64 (d, 1H, J=9.6 Hz), 5.39 (d, 1H, J=12.1 Hz), 5.83 (d, 1H, J=11.7 Hz), 5.98 (br s 1H), 8.02 (s, 1H). $^{13}$C NMR (125 MHz, MeOD) δ 10.9, 16.3, 20.6, 20.8, 20.9, 22.8, 23.2, 25.1, 25.4, 26.6, 30.9, 31.8, 36.1, 37.5, 44.0, 44.1, 54.8, 55.5, 56.3, 69.1, 71.0, 125.3, 155.1, 169.0, 171.8, 172.0, 173.5, 175.7, 178.4. HRMS (FAB) calcd for $C_{31}H_{51}N_4O_8S$ (M+H): 639.3428. Found: 639.3439.

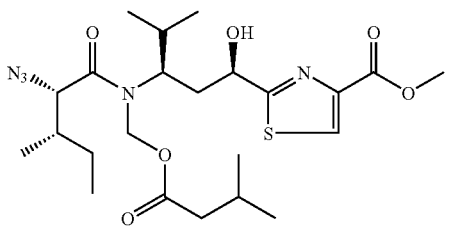 [SMILES: CC[C@H](C)[C@H](N=[N+]=[N-])C(=O)N(COC(=O)CC(C)C)[C@H](C[C@@H](O)c1nc(C(=O)OC)cs1)C(C)C]

1.8 Synthesis of 2-{3-[(2-azido-3-methyl-pentanoyl)-(3-methyl-butyryloxymethyl)-amino]-1-hydroxy-4-methyl-pentyl}-thiazole-4-carboxylic acid methyl ester (15)

A 0.02 M solution of 14 (475 mg, 0.759 mmol) in deoxygenated AcOH/$H_2O$/THF (38.0 mL, 3:1:1, v/v/v) was stirred at rt for 27 h. Addition of 400 mL of toluene followed by concentration and normal-phase HPFC purification (95:5 to 60:40 hexanes:EtOAc) afforded 283 mg (73%) of 15 as an amorphous solid. $[\alpha]_D^{23}$=+55.1 (c=1.0, MeOH). IR: 1095, 1212, 1652, 1735, 2099, 2963 cm$^{-1}$. $^1$H NMR (500 MHz, MeOD): δ 0.88-0.99 (m, 15H), 1.02 (d, 3H, J=6.5 Hz), 1.25-1.35 (m, 1H), 1.72-1.79 (m, 1H), 1.80-1.90 (m, 1H), 1.98-2.09 (m, 2H), 2.10-2.25 (m, 2H), 2.34 (d, 2H, J=7.0 Hz), 3.74 (d, 1H, J=9.5 Hz), 3.89 (s, 3H), 4.47-4.70 (br s, 1H), 4.79 (d, 1H, J=10.5 Hz), 5.48 (d, 1H, J=12.5 Hz), 5.58 (d, 1H, J=10.5 Hz), 8.30 (s, 1H). $^{13}$C NMR (125 MHz, MeOD): δ 11.0, 16.1, 20.4, 20.8, 22.88, 22.91, 26.1, 26.7, 32.0, 36.7, 39.3, 44.2, 52.8, 64.6, 69.6, 129.3, 147.7, 163.3, 173.6, 173.7, 180.2. HRMS (FAB) calcd for $C_{23}H_{37}N_5O_6SNa$ (M+Na): 534.2362. Found: 534.2367.

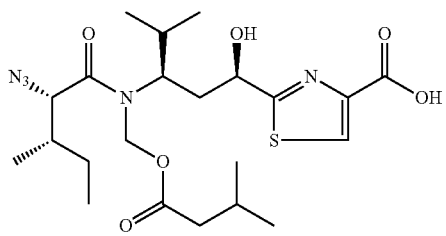 [SMILES: CC[C@H](C)[C@H](N=[N+]=[N-])C(=O)N(COC(=O)CC(C)C)[C@H](C[C@@H](O)c1nc(C(=O)O)cs1)C(C)C]

1.9 Synthesis of 2-{3-[(2-Azido-3-methyl-pentanoyl)-(3-methyl-butyryloxymethyl)-amino]-1-hydroxy-4-methyl-pentyl}-thiazole-4-carboxylic acid (16)

Me$_3$SnOH (736 mg, 4.07 mmol) was added to a 0.020 M solution of methyl ester 15 (260 mg, 0.509 mmol) in dichloroethane (25.0 mL). The reaction mixture was heated to 55° C. for 22 h and then concentrated. Normal-phase HPFC (100:0 to 90:10:1 $CH_2Cl_2$:MeOH:AcOH) followed by reverse-phase HPFC (20:80 to 100:0 MeCN:$H_2O$) and lyophilization afforded 90.0 mg (36%) of 16 as an amorphous solid. $[\alpha]_D^{23}$=+51.5 (c=1.0, MeOH). IR: 1088, 1217, 1651, 1735, 2100, 2964 cm$^{-1}$. $^1$H NMR (500 MHz, MeOD): δ 0.88-0.94 (m, 9H), 0.97 (app t, 6H, J=6.8), 1.03 (d, 3H, J=6.5), 1.31 (sept, 1H, J=7.4), 1.72-1.81 (m, 1H), 1.82-1.90 (br s, 1H), 100-2.09 (m, 2H), 2.10-2.17 (m, 1H), 2.18-2.28 (m, 1H), 2.31 (app t, 2H, J=7.5), 3.75 (d, 1H, J=9.5), 4.44-4.68 (br s, 1H), 4.77 (d, 1H, J=9.5), 5.48 (d, 1H, J=12.5), 5.58 (d, 1H, J=12.5), 8.24 (s, 1H). $^{13}$C NMR (125 MHz, MeOD): δ 10.8, 16.0, 20.3, 20.6, 22.71, 22.73, 26.0, 26.5, 32.0, 36.7, 39.1, 44.1, 64.6, 69.5, 128.5, 149.2, 164.7, 173.58, 173.61, 179.5. HRMS (FAB) calcd for $C_{22}H_{35}N_5O_6SNa$ (M+Na): 520.2206. Found: 520.2200.

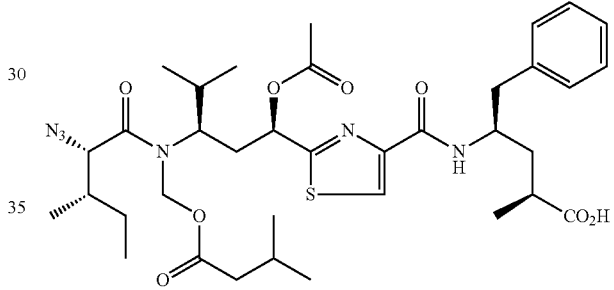

1.10 Synthesis of 4-[(2-{1-acetoxy-3-[(2-azido-3-methyl-pentanoyl)-(3-methyl-butyryloxymethyl)-amino]-4-methyl-pentyl}-thiazole-4-carbonyl)-amino]-2-methyl-5-phenyl-pentanoic acid (8)

Acid 16 (39.0 mg, 0.0784 mmol) was added to a 0.070 M solution of pentafluorophenol (2.0 mg, 0.118 mmol) and 1,3-diisopropylcarbodiimide (13.4 μL, 0.0862 mmol) in $CH_2Cl_2$ at 0° C. The reaction mixture was warmed to rt, stirred for 24 h, and concentrated. EtOAc (10 mL) was added, and the crude product was filtered with rinsing of the reaction vessel with EtOAc. The filtrate was concentrated, and the crude material was used without further purification. DMF (1.00 mL, 0.080 M) was added to the crude product at 0° C., followed by 17 (57.0 mg, 0.235 mmol) and i-Pr$_2$EtN (68.0 μL, 0.392 mmol). The reaction mixture was allowed to warm to rt, stirred for 24 h at rt, and concentrated. Normal-phase HPFC purification (100:0 to 95:5 EtOAc:MeOH) afforded 32.0 mg of product containing trace amounts of i-Pr$_2$EtN. The product mixture (0.181 mmol) was dissolved in pyridine (1.80 mL), cooled to 0° C., and acetic anhydride (0.140 mL, 1.45 mmol) was added. The reaction mixture was allowed to warm to rt over 2 h and was stirred at rt for 22 h. The reaction mixture was then cooled to 0° C., and a 1:1 mixture of deoxygenated $H_2O$/dioxane (0.5 mL) was added. The mixture was allowed to warm to rt and was stirred for 14 h at rt. The solvent was removed under reduced pressure. Reverse-phase HPFC (20:

80 to 100:0 MeCN:H$_2$O) followed by lyophilization afforded 51.0 mg (39%, over three steps) of 8 as an amorphous solid. $[\alpha]_D^{23}$=+61.4 (c=1, MeOH). IR: 1218, 1669, 1739, 2099, 2964 cm$^{-1}$. $^1$H NMR (500 MHz, MeOD): δ 0.87 (app t, 6H, J=6.8 Hz), 0.92 (d, 3H, J=6.5 Hz), 0.93 (d, 3H, J=6.5 Hz), 0.98 (t, 3H, J=7.3 Hz), 1.10 (d, 3H, J=6.5 Hz), 1.17 (d, 3H, J=7.0 Hz), 1.25-1.35 (m, 1H), 1.62-1.69 (m, 1H), 1.72-1.80 (m, 1H), 1.86-1.94 (m, 1H), 1.94-2.04 (m, 2H), 2.06-2.16 (m, 3H), 2.17 (s, 3H), 2.28-2.40 (m, 1H), 2.48-2.58 (m, 2H), 2.91 (d, 2H, J=6.5 Hz), 3.72 (d, 1H, J=9.5 Hz), 4.32-4.41 (m, 1H), 4.41-4.54 (br s, 1H), 5.46 (d, 1H, J=12.5 Hz), 5.59 (d, 1H, J=12.5 Hz), 5.90 (dd, 1H, J=2.0, 11.0 Hz), 7.16 (app sextet, 1H, J=4.5 Hz), 7.23 (app d, 4H, J=4.5 Hz), 8.10 (s, 1H). $^{13}$C NMR (125 MHz, MeOD) δ 10.9, 16.2, 18.7, 20.1, 20.8, 20.9, 22.8, 22.9, 26.1, 26.8, 32.2, 35.8, 36.3, 38.0, 39.4, 42.3, 44.3, 50.9, 64.6, 70.7, 125.6, 127.5, 129.4, 130.6, 139.5, 150.9, 162.8, 170.9, 172.0, 173.21, 173.24, 180.0. HRMS (FAB) calcd for C$_{36}$H$_{52}$N$_6$O$_8$NaS (M+Na): 751.3465. Found: 751.3456.

added. The mixture was stirred for 20 h at rt and concentrated. Reverse-phase HPFC (20:80 to 100:0 MeCN:H$_2$O) followed by lyophilization afforded 9.3 mg (48%) of 6 as an amorphous solid. $[\alpha]_D^{23}$=−2.0 (c=0.6, MeOH). IR: 1226, 1496, 1542, 1741, 2964 cm$^{-1}$. $^1$H NMR (500 MHz, MeOD): δ 0.81 (d, 3H, J=6.5 Hz), 0.87 (d, 3H, J=6.5 Hz), 0.89 (d, 3H, J=7.0 Hz), 0.92 (t, 3H, J=7.5 Hz), 0.98 (d, 3H, J=6.5 Hz), 1.06 (d, 3H, J=6.5 Hz), 1.12-1.21 (m, 1H), 1.17 (d, 3H, J=7.0 Hz), 1.58-1.70 (m, 2H), 1.77-1.91 (m, 2H), 1.92-2.05 (m, 3H), 2.06-2.17 (m, 2H), 2.16 (s, 3H), 2.35 (s, 6H), 2.46-2.57 (m, 2H), 2.92 (d, 2H, J=5.5 Hz), 3.11 (q, 2H, J=16.2 Hz), 4.28-4.50 (br s, 1H), 4.32-4.38 (m, 1H), 4.70 (d, 1H, J=8.5 Hz), 5.46 (d, 1H, J=12.0 Hz), 5.87 (d, 1H, J=11.0 Hz), 6.05 (d, 1H, J=12.0 Hz), 7.12-7.18 (m, 1H), 7.19-7.26 (m, 4H), 8.09 (s, 1H). $^{13}$C NMR (125 MHz, MeOD) δ 11.1, 16.6, 19.0, 20.3, 20.8, 20.9, 22.9, 25.5, 26.2, 26.9, 32.4, 35.9, 37.6, 39.1, 39.7, 42.1, 44.5, 45.8, 51.2, 55.2, 62.7, 70.8, 125.6, 127.5, 129.4, 130.6, 139.7, 150.9, 162.7, 170.8, 171.7, 172.0, 173.3, 176.5, 181.8. HRMS (FAB) calcd for C$_{40}$H$_{62}$N$_5$O$_9$S (M+H): 788.4268. Found: 788.4256.

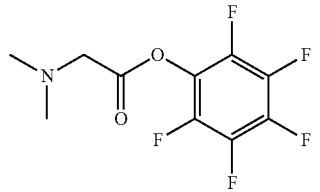 [SMILES: CN(C)CC(=O)Oc1c(F)c(F)c(F)c(F)c1F]

1.11 Synthesis of dimethylamino-acetic acid pentafluorophenyl ester (18)

To a 0.40 M solution of N,N-dimethylglycine (82.0 mg, 0.800 mmol) in EtOAc (2.00 mL, filtered through activated alumina) were added pentafluorophenol (162 mg, 0.880 mmol) and 1,3-dicyclohexylcarbodiimide (182 mg, 0.88 mmol). The reaction mixture was stirred for 12 h at rt at which time it was filtered (washing with EtOAc) and concentrated. Ester 18 was used immediately without further purification.

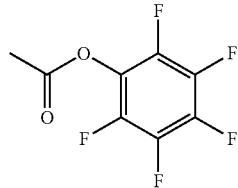

1.13 Synthesis of acetic acid pentafluorophenyl ester (19)

To a 0.40 M solution of acetic acid (46 μL, 0.800 mmol) in EtOAc (2.00 mL, filtered through activated alumina) were added pentafluorophenol (162 mg, 0.880 mmol) and 1,3-dicyclohexylcarbodiimide (182 mg, 0.88 mmol). The reaction mixture was stirred for 12 h at rt at which time it was filtered (washing with EtOAc) and concentrated. Ester 19 was used immediately without further purification.

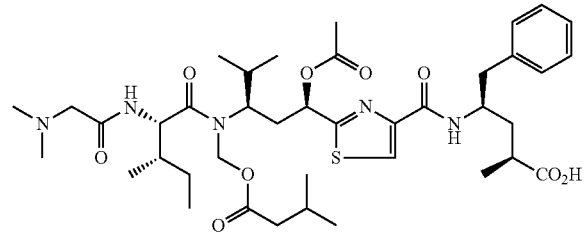 [SMILES: CC[C@H](C)[C@H](NC(=O)CN(C)C)C(=O)N(COC(=O)CC(C)C)[C@H](C[C@@H](OC(C)=O)c1nc(C(=O)N[C@@H](Cc2ccccc2)C[C@H](C)C(=O)O)cs1)C(C)C]

1.12 Synthesis of 4-[(2-{1-acetoxy-3-[[2-(2-dimethylamino-acetylamino)-3-methyl-pentanoyl]-(3-methyl-butyryloxymethyl)-amino]-4-methyl-pentyl}-thiazole-4-carbonyl)-amino]-2-methyl-5-phenyl-pentanoic acid (6)

Pd/C (10 wt %, 8.7 μg) and azide 8 (18.0 mg, 0.0247 mmol) were added to a 0.20 M solution of 18 (0.0988 mmol) in 0.40 mL of EtOAc (filtered through activated alumina). The reaction mixture was stirred under a hydrogen atmosphere for 26 h and then filtered through a plug of Celite with washing of the filter pad with EtOAc. The filtrate was concentrated, and a 1:1 mixture of deoxygenated H$_2$O/dioxane (4.0 mL) was

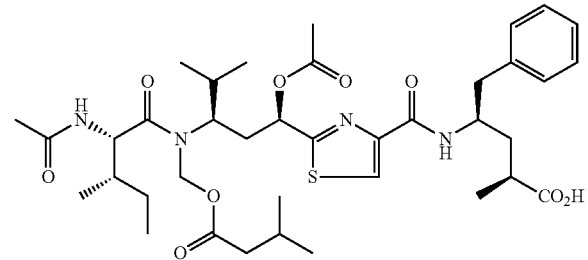 [SMILES: CC[C@H](C)[C@H](NC(C)=O)C(=O)N(COC(=O)CC(C)C)[C@H](C[C@@H](OC(C)=O)c1nc(C(=O)N[C@@H](Cc2ccccc2)C[C@H](C)C(=O)O)cs1)C(C)C]

1.14 Synthesis of 4-[(2-[1-acetoxy-3-[(2-acetylamino-3-methyl-pentanoyl)-(3-methyl-butyryloxymethyl-amino]-4-methyl-pentyl]-thiazole-4-carbonyl)-amino]-2-methyl-5-phenyl-pentanoic acid (7)

Pd/C (10 wt %, 7.0 μg) and azide 8 (15.0 mg, 0.021 mmol) were added to a 0.20 M solution of 19 (0.082 mmol) in 0.40 mL of EtOAc (filtered through activated alumina). The reaction mixture was stirred under a hydrogen atmosphere for 21 h and then filtered through a plug of Celite with washing of the filter pad with EtOAc. The filtrate was concentrated, and a 1:1 mixture of deoxygenated H₂O/dioxane (2.0 mL) was added. The mixture was stirred for 7 h at rt and concentrated. Normal-phase HPFC (99:1 to 90:10 CH₂Cl₂:MeOH) afforded 12.0 mg (77%) of 7 as an amorphous solid. [α]$_D^{23}$=−7.0 (c=0.4, MeOH). IR: 1225, 1554, 1647, 1740, 2876, 2963 cm⁻¹. ¹H NMR (500 MHz, MeOD): δ 0.81 (d, 3H, J=7.0 Hz), 0.86 (d, 3H, J=7.0 Hz), 0.88 (d, 3H, J=7.0 Hz), 0.92 (t, 3H, J=7.5 Hz), 0.95 (d, 3H, J=7.0 Hz), 1.07 (d, 3H, J=6.5 Hz), 1.17 (d, 3H, J=7.5 Hz), 1.12-1.22 (m, 1H), 1.26-1.36 (m, 1H), 1.57-1.69 (m, 2H), 1.80-1.91 (m, 1H), 1.95 (s, 3H), 1.96-2.08 (m, 4H), 2.09-2.16 (m, 1H), 2.16 (s, 3H), 2.25-2.34 (m, 1H), 2.45-2.57 (m, 2H), 2.91 (d, 2H, J=7.0 Hz), 4.32-4.50 (br s, 1H), 4.34-4.42 (m, 1H), 4.62 (d, 1H, J=9.5 Hz), 5.42 (d, 1H, J=12.0 Hz), 5.89 (d, 1H, J=9.5 Hz), 6.13 (d, 1H, J=12.0 Hz), 7.12-7.18 (m, 1H), 7.19-7.25 (m, 4H), 8.10 (s, 1H). ¹³C NMR (125 MHz, MeOD) δ 11.0, 16.4, 18.8, 20.0, 20.8, 20.9, 22.2, 22.87, 22.88, 25.6, 26.9, 32.5, 35.8, 37.2, 38.1, 39.5, 42.3, 44.5, 50.9, 55.6, 70.8, 125.7, 127.5, 129.4, 130.6, 139.5, 150.7, 162.7, 170.9, 172.0, 173.0, 173.3, 176.6, 180.3. HRMS (FAB) calcd for C₃₈H₅₆N₄O₉NaS (M+Na): 767.3666. Found: 767.3648.

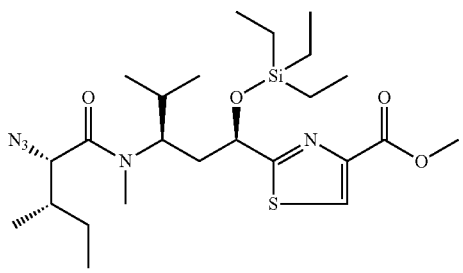 [SMILES: CC[C@H](C)[C@H](N=[N+]=[N-])C(=O)N(C)[C@H](C[C@@H](O[Si](CC)(CC)CC)c1nc(C(=O)OC)cs1)C(C)C]

1.15 Synthesis of 2-{3-[(2-Azido-3-methyl-pentanoyl)-methyl-amino]-4-methyl-1-triethylsilanyloxy-pentyl}-thiazole-4-carboxylic acid methyl ester (21)

A 0.30 M solution of amide 20 (905 mg, 1.77 mmol) in THF (6.0 mL) was cooled to −45° C. and KHMDS (6.02 mL, 3.01 mmol, 0.50 M in toluene) was added. The resulting mixture was stirred for 20 minutes at −45° C. Methyl iodide (754 mg, 5.31 mmol, filtered through activated alumina) was added, and the reaction mixture was allowed to warm to rt over 4.5 h at which time the reaction was quenched with MeOH (5.0 mL). The crude product was diluted with EtOAc (250 mL) and washed with brine (100 mL). The aqueous layer was extracted with EtOAc (2×100 mL). The organic portions were dried, filtered, and concentrated. Normal-phase HPFC (95:5 to 60:40 hexanes:EtOAc) yielded 761 mg of 21 (82%) as an amorphous solid. The ¹H NMR corresponds to a 10:1 mixture of rotamers, with the major isomer reported. [α]$_D^{23}$=+67.5 (c=1.0, CHCl₃). IR: 1094, 1210, 1238, 1645, 1736, 2098, 2877, 2960 cm⁻¹. ¹H NMR (400 MHz, CDCl₃): δ 0.55-0.70 (m, 6H), 0.84 (d, 3H, J=6.8 Hz), 0.85-0.93 (m, 15H), 0.95 (d, 3H, J=6.8 Hz), 1.17-1.29 (m, 1H), 1.60-1.79 (m, 2H), 2.00-2.20 (m, 3H), 2.92 (s, 3H), 3.50 (d, 1H, J=9.6 Hz), 3.89 (s, 3H), 4.37-4.45 (m, 1H), 4.90 (dd, 1H, J=3.6, 6.4 Hz), 8.07 (s, 1H). ¹³C NMR (100 MHz, CDCl₃): δ 4.6, 6.7, 10.6, 15.9, 19.1, 20.0, 25.0, 30.2, 34.9, 40.1, 52.2, 57.3, 63.9, 71.0, 127.4, 146.4, 161.8, 169.5, 178.3. HRMS (FAB) calcd for C₂₄H₄₄N₅O₄SiS (M+H): 526.2883. Found: 526.2877.

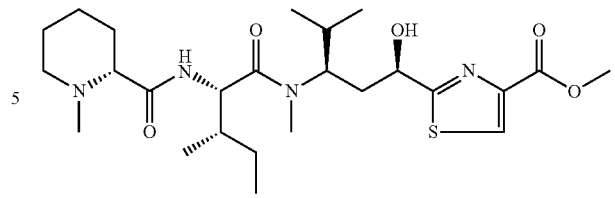

1.16 Synthesis of 2-[1-hydroxy-4-methyl-3-(methyl-{3-methyl-2-[(1-methyl-piperidine-2-carbonyl)-amino]-pentanoyl}-amino)-pentyl]-thiazole-4-carboxylic acid methyl ester (23)

Pd/C (10 wt %, 242 mg) and azide 21 (359 mg, 0.683 mmol) were added to a 0.32 M solution of 22 (2.17 mmol) in 6.80 mL of EtOAc (filtered through activated alumina). The reaction mixture was stirred under a hydrogen atmosphere for 26 h and then filtered through a plug of Celite, with washing of the filter pad with EtOAc. Normal-phase HPFC purification (99:1 to 95:5 EtOAc:MeOH) provided 483 mg of Mep-coupled product. The product was dissolved in 35.0 mL of deoxygenated AcOH/H₂O/THF (3:1:1, v/v/v, 0.02 M) and stirred at rt for 28 h. Concentration followed by normal-phase HPFC purification (98:2 to 85:15 EtOAc:MeOH) afforded 302 mg (87%, over two steps) of 23 as an amorphous solid. The ¹H NMR corresponds to a 7.5:1 mixture of rotamers, with the major isomer reported. [α]$_D^{23}$=−4.8 (c=1.0, MeOH). IR: 1095, 1212, 1238, 1495, 1622, 1722, 2936 cm⁻¹. ¹H NMR (500 MHz, MeOD): δ 0.81 (d, 3H, J=6.5 Hz), 0.91 (t, 3H, J=7.5 Hz), 0.97 (d, 3H, J=6.5 Hz), 0.99 (d, 3H, J=6.5 Hz), 1.16-1.34 (m, 2H), 1.49-1.66 (m, 4H), 1.75 (d, 2H, J=10.5 Hz), 1.77-1.86 (br s, 1H), 1.89-2.01 (m, 2H), 2.02-2.09 (m, 1H), 2.17 (s, 3H), 2.18-2.26 (m, 1H), 2.57 (d, 1H, J=9.0 Hz), 2.85-2.95 (m, 1H), 3.17 (s, 3H), 3.91 (s, 3H), 4.40-4.55 (br s, 1H), 4.68 (d, 1H, J=9.5 Hz), 4.75 (d, 1H, J=9.0 Hz), 8.32 (s, 1H). ¹³C NMR (125 MHz, MeOD): δ 11.2, 16.2, 20.5, 20.7, 24.4, 25.9, 26.3, 31.1, 31.6, 32.1, 37.7, 38.8, 44.9, 52.8, 55.0, 56.7, 69.9, 70.6, 129.3, 147.5, 163.2, 175.4, 175.7, 180.6. HRMS (FAB) calcd for C₂₅H₄₃N₄O₅S (M+H): 511.2954. Found: 511.2947.

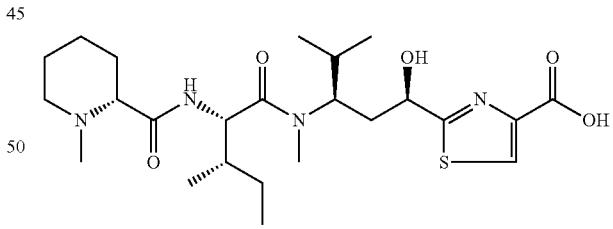

1.17 Synthesis of 2-[1-hydroxy-4-methyl-3-(methyl-{3-methyl-2-[(1-methyl-piperidine-2-carbonyl)-amino]-pentanoyl}-amino)-pentyl]-thiazole-4-carboxylic acid (24)

Me₃SnOH (496 mg, 2.74 mmol) was added to a 0.020 M solution of methyl ester 23 (175 mg, 0.343 mmol) in dichloroethane (17.0 mL). The reaction mixture was heated to 60° C. for 20 h and then concentrated. Column chromatography (100% CH₂Cl₂ to elute tin containing materials followed by 80:20:1 CH₂Cl₂:MeOH:NH₄OH to elute the product) afforded 150 mg (88%) of 24 as an amorphous solid. The ¹H NMR corresponds to a 6:1 mixture of rotamers, with the major isomer reported. $[\alpha]_D^{23}=-17.4$ (c=1.0, MeOH). IR: 1276, 1368, 1471, 1616, 2874, 2961 cm$^{-1}$. $^1$H NMR (500 MHz, d$_6$-DMSO): δ 0.70 (m, 3H), 0.75-0.82 (m, 3H), 0.83-0.90 (m, 6H), 1.04-1.16 (m 1H), 1.17-1.28 (m, 2H), 1.37-1.55 (m, 3H), 1.56-1.72 (m, 3H), 1.73-1.91 (m, 3H), 2.00-2.24 (m, 2H), 2.22 (s, 3H), 2.84 (br s, 1H), 2.94-3.00 (m, 1H), 3.04 (s, 3H), 4.16-4.60 (br s, 1H), 4.49 (d, 1H, J=10.5), 4.56 (app t, 1H, J=9.0), 5.93-6.40 (br s, 1H), 8.05 (s, 1H), 8.25 (s, 1H). $^{13}$C NMR (125 MHz, d$_6$-DMSO): δ 10.0, 14.7, 19.1, 19.5, 19.6, 21.8, 23.58, 23.62, 28.75, 28.8, 35.2, 36.7, 42.6, 52.3, 54.1, 67.1, 67.5, 126.7, 147.8, 162.2, 170.7, 172.0, 177.6. HRMS (FAB) calcd for C$_{24}$H$_{41}$N$_4$O$_5$S (M+H): 497.2798. Found: 497.2793.

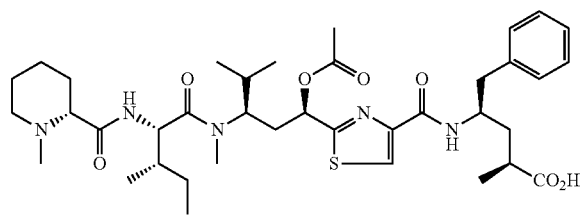 [SMILES: CC[C@H](C)[C@H](NC(=O)[C@H]1CCCCN1C)C(=O)N(C)[C@H](C[C@@H](OC(C)=O)c1nc(C(=O)N[C@@H](Cc2ccccc2)C[C@H](C)C(=O)O)cs1)C(C)C]

1.18 Synthesis of 4-({2-[1-Acetoxy-4-methyl-3-(methyl-{3-methyl-2-[(1-methyl-piperidine-2-carbonyl)-amino]-pentanoyl}-amino)-pentyl]-thiazole-4-carbonyl}-amino)-2-methyl-5-phenyl-pentanoic acid (10)

Acid 24 (34.0 mg, 0.0684 mmol) was added to a solution of pentafluorophenol (19.0 mg, 0.103 mmol) and 1,3-diisopropylcarbodiimide (12.0 µL, 0.0752 mmol) in 0.52 mL of CH$_2$Cl$_2$ at 0° C. The reaction mixture was warmed to rt, stirred for 24 h, and concentrated. EtOAc (10 mL) was added, and the crude product was filtered with rinsing of the reaction vessel with EtOAc. The filtrate was concentrated, and the crude material was used without further purification. DMF (0.270 mL, 0.25 M) was added to the crude product at 0° C., followed by 17 (50.0 mg, 0.205 mmol) and i-Pr$_2$EtN (60.0 µL, 0.342 mmol). The reaction mixture was allowed to warm to rt, stirred for 24 h at rt, and concentrated. Normal-phase HPFC purification (98:2 to 80:20 CH$_2$Cl$_2$:MeOH) followed by reverse-phase HPFC (20:80 to 100:0 MeCN:H$_2$O) afforded 34.0 mg of product containing trace amounts of i-Pr$_2$EtN. The product mixture (34.0 mg, 0.496 mmol) was dissolved in pyridine (0.50 mL), cooled to 0° C., and acetic anhydride (38.0 µL, 0.397 mmol) was added. The reaction mixture was allowed to warm to rt over 2 h and was stirred at rt for 22 h. The reaction mixture was then cooled to 0° C., and a 1:1 mixture of deoxygenated H$_2$O/dioxane (1.6 mL) was added. The mixture was allowed to warm to rt and was stirred for 20 h at rt. The solvent was removed under reduced pressure. Normal-phase HPFC (95:5 to 80:20 CH$_2$Cl$_2$:MeOH) followed by lyophilization afforded 28.0 mg (56%, over three steps) of 10 as an amorphous solid. The $^1$H NMR corresponds to a 16:1 mixture of rotamers, with the major isomer reported. $[\alpha]_D^{23}=-19.2$ (c=0.9, MeOH). IR: 1220, 1495, 1541, 1643, 1712, 2964 cm$^{-1}$. $^1$H NMR (500 MHz, MeOD): δ 0.81 (d, 3H, J=6.5 Hz), 0.92 (t, 3H, J=7.3 Hz), 0.98 (d, 3H, J=6.5 Hz), 1.03 (d, 3H, J=6.5 Hz), 1.16 (d, 3H, J=7.0 Hz), 1.09-1.23 (m, 1H), 1.37-1.41 (m, 1H), 1.56-1.74 (m, 5H), 1.75-1.92 (m, 4H), 1.96-2.05 (m, 1H), 2.15 (s, 3H), 2.31 (s, 3H), 2.23-2.41 (m, 3H), 2.51 (br s, 1H), 2.85 (d, 1H, J=10.5 Hz), 2.92 (d, 2H, J=6.5 Hz), 3.05 (d, 1H, J=11.5 Hz), 110 (s, 3H), 4.30-4.50 (m, 2H), 4.73 (d, 1H, J=8.0 Hz), 5.71 (dd, 1H, J=2.5, 11.0 Hz), 7.13-7.18 (m, 1H), 7.19-7.25 (m, 4H), 8.08 (s, 1H). $^{13}$C NMR (125 MHz, MeOD) δ 11.3, 16.4, 19.1, 20.4, 20.6, 20.9, 23.7, 25.5, 25.5, 30.9, 31.0, 31.1, 35.6, 37.6, 39.5, 39.6, 42.0, 44.2, 51.2, 55.2, 56.4, 69.7, 71.2, 125.1, 127.4, 129.3, 130.6, 139.8, 151.1, 162.7, 171.6, 171.8, 173.6, 175.0, 182.5. HRMS (FAB) calcd for C$_{38}$H$_{57}$N$_5$O$_7$S (M+H): 728.4057. Found: 728.4053.

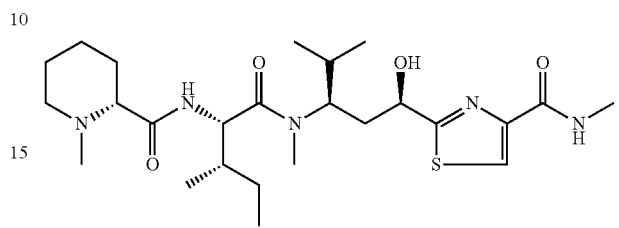

1.19 Synthesis of 1-methyl-piperidine-2-carboxylic acid [1-({1-[2-hydroxy-2-(4-methylcarbamoyl-thiazol-2-yl)-ethyl]-2-methyl-propyl}-methyl-carbamoyl)-2-methyl-butyl]-amide (25)

In a sealed tube, 10.0 mL of a 2.0 M solution of methylamine (5.00 mmol) in THF was added to a 0.02 M solution of 23 (27.0 mg, 0.0529 mmol) in MeOH (2.50 mL). The reaction solution was heated to 100° C. for 21 h. After the solution cooled to rt, the solvent was removed under reduced pressure. Reverse-phase HPFC (20:80 to 100:0 MeCN/H$_2$O) followed by lyophilization provided compound 25 (14.0 mg, 52%) as an amorphous solid. The $^1$H NMR corresponds to a 6:1 mixture of rotamers, with the major isomer reported. $[\alpha]_D^{23}=-2.9$ (c=1.0, MeOH). 1R: 1070, 1499, 1551, 1646, 2876, 2961 cm$^{-1}$. $^1$H NMR (500 MHz, MeOD): δ 0.83 (d, 3H, J=6.5 Hz), 0.90 (t, 3H, J=7.5 Hz), 0.966 (d, 3H, J=6.5 Hz), 0.974 (d, 3H, J=6.5 Hz), 1.15-1.25 (m, 1H), 1.25-1.32 (m, 1H), 1.48-1.66 (m, 4H), 1.72 (d, 2H, J=10.5 Hz), 1.81-1.99 (m, 3H), 2.00-2.10 (m, 1H), 2.16 (s, 3H), 2.19-2.37 (m, 1H), 2.53-2.58 (m, 1H), 2.87-2.94 (m, 1H), 2.92 (s, 3H), 3.17 (s, 3H), 4.16-4.58 (br s, 1H), 4.64 (dd, 1H, J=2.3, 10.3 Hz), 4.72 (d, 1H, J=9.0 Hz), 8.06 (s, 1H). $^{13}$C NMR (125 MHz, MeOD) δ 11.1, 16.1, 20.5, 20.6, 24.4, 25.9, 26.3, 26.4, 31.3, 31.7, 37.8, 38.8, 44.8, 55.4, 56.7, 70.0, 70.6, 124.2, 151.0, 164.4, 175.3, 175.7, 179.4. HRMS (FAB) calcd for C$_{25}$H$_{44}$N$_5$O$_4$S (M+H): 510.3114. Found: 510.3098.

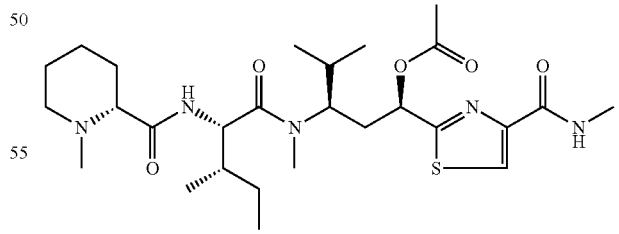

1.20 Synthesis of acetic acid 4-methyl-1-(4-methylcarbamoyl-thiazol-2-yl)-3-(methyl-{3-methyl-2-[(1-methyl-piperidine-2-carbonyl)-amino]-pentanoyl}-amino)-pentyl ester (11)

A 0.050 M solution of 25 (12.0 mg, 0.0235 mmol) in pyridine (0.500 mL) was cooled to 0° C., and acetic anhydride (18.0 μL, 0.188 mmol) was added. The reaction mixture was allowed to warm to rt over 2 h and was stirred at rt for 21 h. The solvent was removed under reduced pressure. Reverse-phase HPFC (20:80 to 100:0 MeCN:H$_2$O) followed by lyophilization afforded 9.3 mg (72%) of 11 as an amorphous solid. The $^1$H NMR corresponds to a 23:1 mixture of rotamers, with the major isomer reported. [α]$_D^{23}$=−2.2 (c=0.6, MeOH). IR: 1221, 1498, 1549, 1643, 1755, 2937 cm$^{−1}$. $^1$H NMR (500 MHz, MeOD): δ 0.80 (d, 3H, J=7.0 Hz), 0.92 (t, 3H, J=7.5 Hz), 0.98 (d, 3H, J=7.0 Hz), 1.02 (d, 3H, J=6.5 Hz), 1.13-1.22 (m, 1H), 1.24-1.34 (m, 1H), 1.49-1.67 (m, 4H), 1.72-1.78 (m, 2H), 1.79-1.91 (m, 2H), 2.07 (dt, 1, J=3.0, 11.5 Hz), 2.15 (s, 3H), 2.18 (s, 3H), 2.22-2.31 (m, 1H), 2.34-2.41 (m, 1H), 2.56 (dd, 1H, J=2.5, 11.0 Hz), 2.90-2.95 (m, 1H), 2.94 (s, 3H), 3.11 (s, 3H), 4.40-4.51 (br s, 1H), 4.74 (d, 1H, J=8.0 Hz), 5.70 (dd, 1H, J=2.5, 11.5 Hz), 8.14 (s, 1H). $^{13}$C NMR (125 MHz, MeOD) δ 11.2, 16.4, 20.4, 20.6, 20.9, 24.4, 25.6, 26.3, 26.4, 31.1, 31.7, 35.7, 37.7, 44.9, 54.9, 56.7, 70.6, 71.2, 125.0, 150.9, 163.9, 171.82, 171.83, 175.3, 175.6. HRMS (FAB) calcd for C$_{27}$H$_{46}$N$_5$O$_5$S (M+H): 552.3220. Found: 552.3218.

1.21 Synthesis of (+)-2-[(S$_S$,1R)-1-Hydroxy-4-methyl-3-(2-methyl-propane-2-sulfinylimino)-pentyl]-thiazole-4-carboxylic acid ethyl ester (31)

A 0.9 M solution of i-Pr$_2$NH (0.669 mL, 4.76 mmol) in Et$_2$O (5.5 mL) was cooled to 0° C. and n-BuLi (1.69 mL, 4.17 mmol, 2.47 M solution in hexanes) was added. The solution was stirred for 20 min at 0° C. and then cooled to −78° C. A solution of sulfinyl ketimine 26 (0.339 g, 1.79 mmol) in Et$_2$O (3.6 mL) was added, and the reaction mixture was stirred for 30 min at −78° C. Chlorotitanium triisopropoxide (0.744 mL, 3.57 mmol) was then added, and the reaction mixture was stirred for an additional 45 min at −78° C. Aldehyde 30 (0.220 g, 1.19 mmol) was added in one portion, and the solution was stirred at −78° C. for 46 h. The solution was neutralized using a 4:1 (v/v) solution of THF/AcOH (2.5 mL) followed by addition of H$_2$O (15 mL). The resulting mixture was warmed to rt and filtered through Celite, washing the filter cake thoroughly with EtOAc. The solution was washed once with brine, dried over MgSO$_4$, filtered, and concentrated. NMR analysis on the unpurified material established a 93:7 ratio of diastereomers. HPFC purification (98:2 to 80:20 MTBE:Et$_2$O) produced a ~5.3:1 mixture of the pure major diastereomer 31 and starting sulfinyl ketimine 26 as a yellow oil. The mixture was further reacted without additional purification.

A small sample was further purified by HPFC (90:10 to 80:20 toluene:EtOAc) for characterization purposes and was isolated as a yellow oil. [α]$_D^{25}$=+67.3 (c=1.0, CHCl$_3$). IR (film): 1476, 1625, 1732, 2871, 2931, 2970, 3220 cm$^{−1}$. $^1$H NMR (500 MHz, CDCl$_3$): δ 1.15 (app t, 6H, J=8.5 Hz), 1.25 (s, 9H), 1.34 (t, 3H, J=7.0 Hz), 2.75-2.85 (m, 1H), 3.22-3.32 (m, 2H), 4.35 (q, 2H, J=7.0 Hz), 5.08 (m, 1H), 6.56 (d, 1H, J=8.5 Hz), 8.06 (s, 1H). $^{13}$C NMR (125 MHz, CDCl$_3$): δ 14.2, 20.0, 20.8, 22.3, 38.8, 43.7, 58.3, 61.2, 67.3, 127.6, 147.1, 161.3, 178.1, 187.4. HRMS (FAB) calcd. for C$_{16}$H$_{26}$N$_2$O$_4$NaS$_2$ (M+Na): 397.1232. Found 397.1229.

1.22 Synthesis of (+)-2-[(S$_S$,1R,3R)-1-Hydroxy-4-methyl-3-(2-methyl-propane-2-sulfinylamino)-pentyl]-thiazole-4-carboxylic acid ethyl ester (32)

A solution of the product mixture containing β-hydroxy imine 31 (~0.943 mmol) and imine 26 (~0.178 mmol) in THF (3.50 mL) was cooled to −78° C. Ti(OEt)$_4$ (0.469 mL, 2.24 mmol) was added, followed by NaBH$_4$ (0.0847 g, 2.24 mmol), and the solution was stirred at −78° C. for 12 h. The solution was acidified using a 4:1 (v/v) solution of THF/AcOH (3.2 mL) followed by addition of EtOH (2 mL) and H$_2$O (10 mL). The solution was warmed to rt and diluted with EtOAc. The mixture was washed once with brine, and the aqueous fraction was extracted once with EtOAc. The combined organic fractions were dried with Na$_2$SO$_4$, filtered, and concentrated. NMR analysis on the unpurified material established a 92:8 ratio of diastereomers. HPFC purification (100% EtOAc) produced 0.332 g (74%, over two steps) of the pure major diastereomer 32 as a colorless oil. [α]$_D^{25}$=+103.2 (c=1.0, CHCl$_3$). IR (film): 1474, 1718, 2868, 2929, 2960, 3283 cm$^{−1}$. $^1$H NMR (500 MHz, CDCl$_3$): δ 0.90 (d, 3H, J=6.8 Hz), 0.93 (d, 3H, J=6.8 Hz), 1.29 (s, 9H), 1.40 (t, 3H, J=7.1 Hz), 1.70 (doublet of septets, 1H, J=2.3, 6.8 Hz), 1.91 (ddd, 1H, J=3.6, 11.5, 14.7 Hz), 2.30 (ddd, 1H, J=3.0, 11.8, 14.7 Hz), 3.30 (d, 1H, J=8.5 Hz), 3.40-3.47 (m, 1H), 4.38-4.45 (m, 2H), 5.18 (ddd, 1H, J=3.1, 6.7, 11.6 Hz), 5.48 (d, 1H, J=6.7 Hz), 8.11 (s, 1H). $^{13}$C NMR (125 MHz, CDCl$_3$): δ 14.4, 17.3, 19.7, 23.0, 33.9, 40.6, 56.3, 58.5, 61.3, 67.8, 127.4, 147.0, 161.6, 177.6. HRMS (FAB) calcd. for C$_{16}$H$_{28}$N$_2$O$_4$NaS$_2$ (M+Na): 399.1388. Found 399.1389.

1.23 Synthesis of (+)-2-[(S$_S$,1R,3R)-4-Isopropyl-3-(2-methyl-propane-2-sulfinyl)-[1,3]oxazinan-6-yl]-thiazole-4-carboxylic acid ethyl ester (33)

A 0.1 M solution of N-sulfinyl amino alcohol 32 (0.575 g, 1.53 mmol) in toluene (15.3 mL) with paraformaldehyde (0.917 g, 30.5 mmol) was heated in a sealed vessel at 70° C. with stirring for 50 h. After cooling to rt, the mixture was filtered through Celite, washing the filter cake thoroughly with toluene. The solution was concentrated and purified via HPFC (88:12 to 30:70 CH$_2$Cl$_2$:EtOAc) to afford 0.518 g of tetrahydrooxazine 33 (87%) as a foamy yellow solid. [α]$_D^{25}$=+108.4 (c=1.0, CHCl$_3$). IR (film): 1011, 1076, 1087, 1163, 1195, 1474, 1729, 2957, 2979 cm$^{−1}$. $^1$H NMR (500 MHz, CDCl$_3$): δ 1.01 (d, 3H, J=6.8 Hz), 1.02 (d, 3H, J=6.8 Hz), 1.17 (s, 9H), 1.35 (t, 3H, J=7.1 Hz), 2.08-2.16 (m, 1H), 2.28-2.40 (m, 1H), 2.31 (d, 1H, J=14.3 Hz), 3.02 (dd, 1H, J=4.7, 10.1 Hz), 4.37 (q, 2H, J=7.1 Hz), 4.72 (d, 1H, J=11.6 Hz), 5.14 (d, 1H, J=11.6 Hz), 5.20 (dd, 1H, J=2.5, 11.5 Hz), 8.11 (s, 1H). $^{13}$C NMR (125 MHz, CDCl$_3$): δ 14.3, 20.5, 20.7, 22.8, 27.5, 32.6, 59.2, 61.3, 62.7, 71.4, 71.6, 127.8, 146.5, 161.3, 173.3. HRMS (FAB) calcd. for C$_{17}$H$_{29}$N$_2$O$_4$S$_2$ (M+H): 389.1569. Found 389.1566.

1.24 Synthesis of (+)-(1R,3R)-2-(1-Hydroxy-4-methyl-3-methylamino-pentyl)-thiazole-4-carboxylic acid ethyl ester (35)

To a 0.18 M solution of tetrahydrooxazine 33 (0.200 g, 0.514 mmol) in 9:1 MeCN/EtOH (2.9 mL) with MP-BH$_3$CN (2.52 mmol/g, 0.204 g, 0.514 mmol) was added dropwise HCl (4.0 M in 1,4-dioxane, 0.515 mL, 2.06 mmol) with stirring. Stirring was continued for 3 h at rt, and then the solution was concentrated and purified by HPFC (95:5:1 to 90:10:1 CH$_2$Cl$_2$:EtOH:NH$_4$OH). The product fractions were concentrated, diluted with EtOAc, and washed once with sat. NaHCO$_3$ (aq) to remove excess ammonia salts. The aqueous fraction was back-extracted once with EtOAc. The combined organic fractions were dried with Na$_2$SO$_4$ and concentrated to afford 0.143 g of N-methyl tubuvaline ethyl ester 35 (97%) as a foamy solid. [α]$_D^{25}$=+70.5 (c=0.8, CHCl$_3$). IR (film): 1087, 1232, 1315, 1492, 1713, 2947, 3119 cm$^{−1}$. $^1$H NMR (500 MHz, d$_4$-MeOD): δ 0.89 (d, 3H, J=6.8 Hz), 0.90 (d, 3H, J=6.8 Hz), 1.39 (t, 3H, J=7.0 Hz), 1.88-2.04 (m, 3H), 2.38 (s, 3H), 2.43-2.48 (m, 1H), 4.38 (q, 2H, J=7.0 Hz), 5.14-5.18 (m, 1H), 8.32 (s, 1H). $^{13}$C NMR (125 MHz, d$_3$-MeCN): δ 14.6, 17.3, 20.1, 28.8, 33.1, 33.9, 61.9, 63.5, 72.1, 128.6, 148.2, 162.4, 180.8. HRMS (FAB) calcd. for C$_{13}$H$_{23}$N$_2$O$_3$S (M+H): 287.1429. Found 287.1427.

1.25 Synthesis of 2-{(1R,3R)-1-[(2S,3S)-2-tert-Butoxycarbonylamino-3-methyl-pentanoyloxy]-4-methyl-3-methylamino-pentyl}-thiazole-4-carboxylic acid ethyl ester (36)

A 0.1 M solution of N-methyl tubuvaline ethyl ester 35 (0.305 g, 1.06 mmol), 1-hydroxybenzotriazole (HOBt) (0.146 g, 1.08 mmol), and Boc-Ile-OH (0.267 g, 1.11 mmol) in CH$_2$Cl$_2$ (10.6 mL) was cooled in a salted ice-water bath. PS-CCD (1.38 mmol/g, 0.920 g, 1.27 mmol) was added with stirring, and the bath was warmed to rt. Stirring was continued for 14 h, the solution was filtered, and the resin was washed with CH$_2$Cl$_2$. The filtrate was then concentrated, diluted with EtOAc, and washed once with sat. NaHCO$_3$ (aq). The aqueous fraction was back-extracted twice with EtOAc, and the combined organic fractions were dried with Na$_2$SO$_4$, filtered, and concentrated to afford intermediate 36, which was taken on without further purification.

A small sample of ester 36 was further purified for characterization purposes. The intermediate was first isolated as the formic acid salt via reverse-phase HPFC (80:20 to 0:100 H$_2$O:MeCN with 0.1% formic acid). The product fractions were concentrated, diluted with EtOAc, and washed once with sat. NaHCO$_3$ (aq) to provide the free amine. The organic fraction was dried with Na$_2$SO$_4$ and concentrated to afford pure ester 32 as an amorphous solid. $^1$H NMR (400 MHz, CDCl$_3$): δ 0.81 (d, 3H, J=6.8 Hz), 0.86-0.93 (m, 6H), 0.95 (d, 3H, J=6.8 Hz), 1.11-1.25 (m, 1H), 1.37 (t, 3H, J=7.1 Hz), 1.34-1.48 (m, 2H), 1.40 (s, 9H), 1.82-1.99 (m, 3H), 2.04-2.14 (m, 1H), 2.29-2.36 (m, 1H), 2.34 (s, 3H), 4.39 (q, 2H, J=7.1 Hz), 4.30-4.36 (m, 1H), 5.07 (d, 1H, J=9.2 Hz), 6.37 (dd, 1H, J=3.1, 9.9 Hz), 8.11 (s, 1H). $^{13}$C NMR (100 MHz, CDCl$_3$): δ 11.5, 14.3, 15.5, 16.6, 19.1, 24.7, 28.2, 28.6, 33.6, 36.1, 37.9, 58.2, 60.4, 61.4, 72.0, 79.7, 127.6, 147.1, 155.4, 161.1, 170.9, 171.5. HRMS (FAB) calcd. for C$_{24}$H$_{42}$N$_3$O$_6$S (M+H): 500.2794. Found 500.2787.

1.26 Synthesis of (−)-2-{(1R,3R)-3-[(2S,3S)-(2-tert-Butoxycarbonylamino-3-methyl-pentanoyl)-methylamino]-1-hydroxy-4-methyl-pentyl}-thiazole-4-carboxylic acid ethyl ester (38)

Crude ester 36 (~1.06 mmol) in toluene (10.6 mL, 0.1 M) was heated to 90° C. in a sealed vessel with stirring for 30 h. HPFC purification (88:12 to 0:100 hexanes:EtOAc) afforded 0.492 g of N-methyl carbamate 38 (93%, two steps) as an amorphous solid. The $^1$H NMR spectrum indicated that the product existed as a 7:1 mixture of rotamers, with the major isomer reported. [α]$^{25}_D$=−11.7 (c=1.0, CHCl$_3$). IR (film): 1016, 1094, 1166, 1206, 1234, 1366, 1495, 1617, 1713, 2875, 2934, 2965, 3325 cm$^{-1}$. H NMR (500 MHz, d$_4$-MeOD): δ 0.84 (d, 3H, J=7.4 Hz), 0.91 (t, 3H, J=7.4 Hz), 0.94-0.99 (m, 6H), 1.39 (t, 3H, J=7.1 Hz), 1.42 (s, 9H), 1.58-1.69 (m, 1H), 1.77-1.87 (m, 2H), 1.88-1.95 (m, 1H), 2.14-2.24 (m, 1H), 3.15 (s, 3H), 4.38 (q, 2H, J=7.1 Hz), 4.41 (d, 1H, J=8.8 Hz), 4.44-4.57 (br s, 1H), 4.63-4.68 (m, 1H), 8.30 (s, 1H). $^{13}$C NMR (125 MHz, d$_4$MeOD): δ 11.3, 14.7, 16.2, 20.3, 20.6, 25.7, 28.8, 31.1, 37.6, 38.7, 56.8, 58.1, 62.5, 69.9, 80.5, 129.1, 147.8, 158.0, 162.8, 176.5, 180.5. HRMS (FAB) calcd. for C$_{24}$H$_{41}$N$_3$O$_6$NaS (M+Na): 522.2614. Found 522.2605.

1.27 Synthesis of (−)-2-[(1R,3R)-1-Hydroxy-4-methyl-3-(methyl-{(2S,3S)-3-methyl-2-[((1R)-1-methyl-piperidine-2-carbonyl)-amino]-pentanoyl}-amino)-pentyl]-thiazole-4-carboxylic acid (39)

To a 0.1 M solution of carbamate 38 (0.445 g, 0.891 mmol) in CH$_2$Cl$_2$ (9.00 mL) was added an equal volume of TFA (9.00 mL) with stirring for 1 h. The solution was then concentrated, diluted with EtOAc, and washed once with sat. NaHCO$_3$ (aq). The aqueous fraction was back-extracted twice with EtOAc, and the combined organic fractions were dried with Na$_2$SO$_4$, filtered, and concentrated to afford the Boc-deprotected free amine of 38, which was taken on to the next step without further purification. To this amine in CH$_2$Cl$_2$ (0.1 M, 9.00 mL) was added HOBt (0.122 g, 0.908 mmol) and D-Mep$^{12}$ (0.134 g, 0.935 mmol). The mixture was then cooled in a salted ice-water bath with stirring and PS-CCD (1.38 mol/g, 0.775 g, 1.07 mmol) was added. The bath was warmed to rt, and stirring was continued for 14 h. The mixture was then filtered, the resin was washed with CH$_2$Cl$_2$, and the filtrate was concentrated. The crude mixture was then diluted with EtOAc, and washed once with sat. NaHCO$_3$ (aq). The aqueous fraction was back-extracted twice with EtOAc, and the combined organic fractions were dried with Na$_2$SO$_4$, filtered, and concentrated to afford the Mep-coupled intermediate, which was taken on without further purification. To the crude intermediate diluted in 1,4-dioxane (0.1 M, 9.00 mL) was added a 0.4 M solution of LiOH (85.3 mg, 3.56 mmol) in degassed H$_2$O (9.00 mL). After stirring for 5 h, the solution was concentrated and HPFC purified (90:10:1 to 70:30:1 CH$_2$Cl$_2$:MeOH:NH$_4$OH) to afford 0.438 g of carboxylic acid 39 (99%, three steps) as an amorphous solid. Spectral data of 39 matched that previously reported.

1.28 Synthesis of (−)-2-[(1R,3R)-1-Acetoxy-4-methyl-3-(methyl-{(2S,3S)-3-methyl-2-[((1R)-1-methyl-piperidine-2-carbonyl)-amino]-pentanoyl}-amino)-pentyl]-thiazole-4-carboxylic acid (40)

A 0.1 M solution of alcohol 39 (23.0 mg, 0.0463 mmol) in pyridine (0.460 mL) was cooled in an ice-water bath and Ac$_2$O (21.9 μL, 0.232 mmol) was added with stirring. The bath was warmed to rt and stirring was continued for 24 h. The solution was then cooled in an ice-water bath and a 1:1 (v/v) solution of degassed H$_2$O/dioxane (2 mL) was added. The bath was warmed to rt and stirring was continued for 22 h. Concentration, followed by HPFC purification (80:20:1 CH$_2$Cl$_2$:MeOH:NH$_4$OH), afforded 24.3 mg of acetate 40 (97%) as an amorphous solid. [α]$^{25}_D$=−14.8 (c=0.8, MeOH). IR (film): 1222, 1369, 1470, 1593, 1639, 1747, 2874, 2961 cm$^1$. $^1$H NMR (500 MHz, d$_6$-DMSO): δ 0.67 (d, 3H, J=6.6 Hz), 0.82 (t, 3H, J=7.4 Hz), 0.86 (d, 3H, J=6.7 Hz), 0.91 (d, 3H, J=6.5 Hz), 0.99-1.10 (m, 1H), 1.10-1.22 (m, 1H), 1.29-1.40 (m, 1H), 1.40-1.51 (m, 2H), 1.52-1.58 (m, 1H), 1.58-1.67 (m, 2H), 1.71-1.82 (m, 2H), 1.97-2.04 (m, 1H), 2.08 (s, 3H), 2.11 (s, 3H), 2.12-2.17 (m, 1H), 2.17-2.25 (m, 1H), 2.52-2.56 (m, 1H), 2.84-2.89 (m, 1H), 2.97 (s, 3H), 4.23-4.43 (br s, 1H), 4.60 (app t, 1H, J=8.8 Hz), 5.53 (dd, 1H, J=2.4, 11.0 Hz), 7.69 (d, 1H, J=9.2 Hz), 8.32 (s, 1H). $^{13}$C NMR (125 MHz, d$_6$-DMSO): δ 10.6, 15.4, 19.4, 20.0, 20.6, 22.4, 23.9, 24.3, 28.9, 29.4, 33.9, 35.8, 43.4, 52.5, 54.5, 55.1 (br s), 67.7, 69.6, 126.8, 150.1, 162.9, 169.1, 169.7, 171.5, 172.7. HRMS (FAB) calcd. for C$_{26}$H$_{43}$N$_4$O$_6$S (M+H): 539.2903. Found 539.2884.

Example 2

2.1 Cell Culture and Growth Inhibition Assay

Cell lines were obtained from the American Type Culture Collection (ATCC) and the German Collection of Microorganisms and Cell Cultures (DSMZ). All cell lines were cultivated under conditions recommended by their respective depositors. Growth inhibition was measured in microtiter plates. Aliquots of 120 μl of the suspended cells (50,000/mL) were given to 60 μL of a serial dilution of the inhibitor and incubated at 37° C. and 10% $CO_2$. After 5 days, when control cells had grown to confluence state, the metabolic activity in each well was determined using an MTT assay. $IC_{50}$ values were defined as the analogue concentration that showed only 50% of the activity of the control wells.

2.2 Fluorescence Staining $PtK_2$ cells (ATCC CCL-56) were grown on glass coverslips (13 mm diameter) in four-well plates. Exponentially growing cells were incubated with the analogues for 18 hours. Cells were then fixed with cold (−20° C.) acetone/methanol (1:1) for 10 minutes. For labeling the microtubules, cells were incubated with a primary monoclonal antibody against α-tubulin (1:500; Sigma), then with a secondary goat anti-mouse IgG antibody conjugated with Alexa Fluor 488 (1:200; Molecular Probes) at 37° C. for 45 minutes. Nuclei and chromosomes were stained with DAPI (1 μg/mL). The cells were washed with PBS between all incubations. The coverslips were mounted using Prolong Antifade Gold (Molecular Probes), and viewed with a Zeiss Axiophot fluorescence microscope using appropriate filter sets.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed:

1. A compound of the formula which is selected from:

(II)

(III)

wherein
$R^1$ is a nitrogen containing moiety selected from an azide, a hydrazide and a hydrazone;
$R^2$ is selected from H, substituted alkyl and substituted or unsubstituted heteroalkyl;
$R^3$ is selected from H, acyl, substituted or unsubstituted alkyl, and substituted or unsubstituted heteroalkyl;
$R^6$ is a member selected from H, substituted or unsubstituted alkyl and substituted or unsubstituted heteroalkyl;
$R^{6a}$, $R^{7a}$ and $R^8$ are independently selected from H, substituted or unsubstituted alkyl and substituted or unsubstituted heteroalkyl; and
Y is a member selected from $(CH_2)_n COOR^{4a}$, $(CH_2)_n OR^4$; and $(CH_2)_n NR^4 R^5$
  wherein
    n is an integer from 0 to 10;
    $R^{4a}$ is selected from H, substituted or unsubstituted alkyl and substituted or unsubstituted heteroalkyl; and
    $R^4$ and $R^5$ are independently selected from H, substituted or unsubstituted alkyl and substituted or unsubstituted heteroalkyl;
or a pharmaceutically acceptable salt or prodrug thereof.

2. A compound of the formula:

wherein
$R^2$ is selected from H, substituted alkyl and substituted or unsubstituted heteroalkyl;
$R^3$ is selected from H, acyl, substituted or unsubstituted alkyl, or substituted or unsubstituted heteroalkyl;
$R^{6a}$ is selected from H, substituted or unsubstituted alkyl and substituted or unsubstituted heteroalkyl; and
Y is a member selected from $(CH_2)_n COOR^{4a}$, $(CH_2)_n OR^4$; and $(CH_2)_n NR^4 R^5$
  wherein
    n is an integer from 0 to 10;
    $R^{4a}$ is selected from H, substituted or unsubstituted alkyl and substituted or unsubstituted heteroalkyl; and
    $R^4$ and $R^5$ are independently selected from H, substituted or unsubstituted alkyl and substituted or unsubstituted heteroalkyl;
or a pharmaceutically acceptable salt or prodrug thereof.

3. The compound according to claim 2 wherein Y is $(CH_2)_n COOR^{4a}$; and n is an integer from 0 to 10.

4. The compound according to claim 2 wherein $R^{6a}$ comprises an amino acid residue.

5. A pharmaceutical formulation comprising a compound according to claim 1 and a pharmaceutically acceptable diluent.

6. A method of treating colon cancer and cervix cancer in a subject, said method comprising administering to said subject a therapeutically effective amount of a compound according to claim 1.

7. A compound according to claim 1 of the formula:

(IV)

wherein
R¹ᵃ and R²ᵃ are independently selected from H, substituted or unsubstituted alkyl, substituted or unsubstituted heteroalkyl, substituted or unsubstituted aryl, substituted or unsubstituted heteroaryl and substituted or unsubstituted heteroarylalkyl.

8. A compound according to claim 7 of the formula:

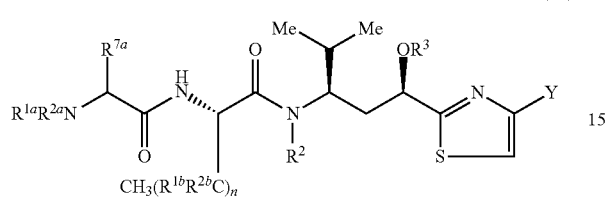
(VI)

wherein R¹ᵇ and R²ᵇ are independently selected from H and unsubstituted alkyl.

9. A compound according to claim 7 of the formula:

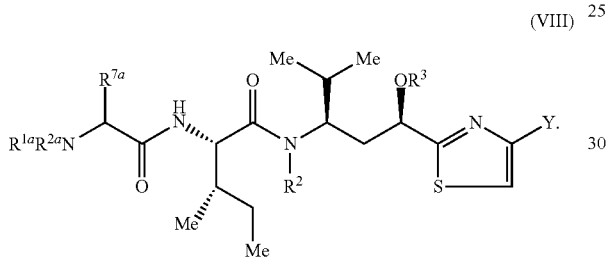
(VIII)

10. A compound according to claim 1 of the formula:

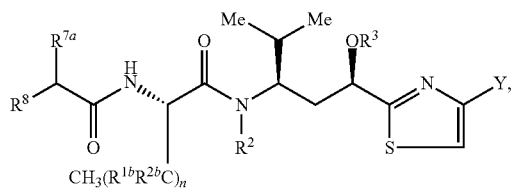
(V)

wherein R¹ᵇ and R²ᵇ are independently selected from H and unsubstituted alkyl.

11. A compound according to claim 1 of the formula:

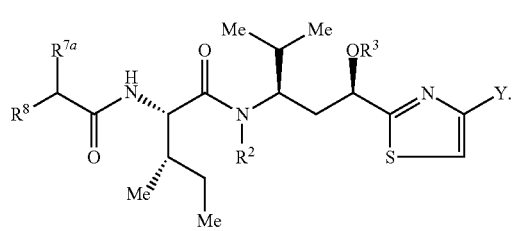
(VII)

12. The compound according to claim 1, which is selected from

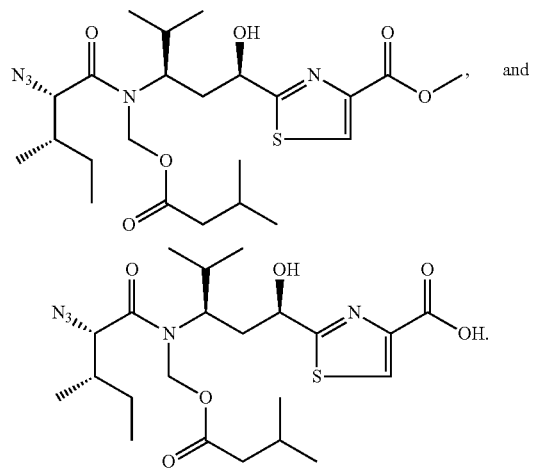
and

13. A compound of the formula which is selected from:

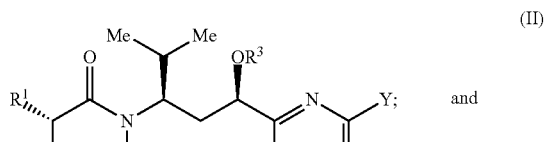
(II)
and

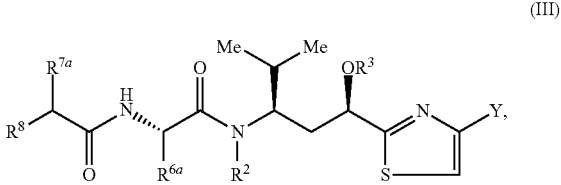
(III)

wherein
R¹ is a nitrogen containing moiety selected from an azide, a hydrazide and a hydrazone;
R² is selected from H, substituted alkyl and substituted or unsubstituted heteroalkyl;
R³ is selected from H, acyl, substituted or unsubstituted alkyl, and substituted or unsubstituted heteroalkyl;
R⁶ is a member selected from H, substituted or unsubstituted alkyl and substituted or unsubstituted heteroalkyl;
R⁶ᵃ, R⁷ᵃ and R⁸ are independently selected from H, substituted or unsubstituted alkyl and substituted or unsubstituted heteroalkyl; and
Y is $(CH_2)_nC(O)NR^4R^5$
wherein
n is an integer from 0 to 10; and
R⁴ and R⁵ are independently selected from H, unsubstituted alkyl and substituted or unsubstituted heteroalkyl;
or a pharmaceutically acceptable salt or prodrug thereof.

14. A compound according to claim 13 of the formula:

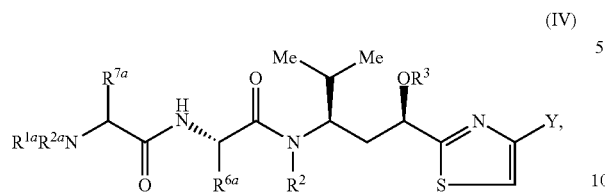

(IV)

wherein
$R^{1a}$ and $R^{2a}$ are independently selected from H, substituted or unsubstituted alkyl, substituted or unsubstituted heteroalkyl, substituted or unsubstituted aryl, substituted or unsubstituted heteroaryl and substituted or unsubstituted heteroarylalkyl.

15. A compound according to claim 13 of the formula:

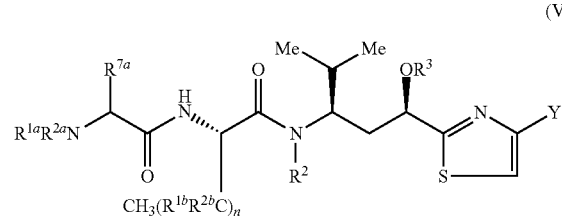

(VI)

wherein $R^{1b}$ and $R^{2b}$ are independently selected from H and unsubstituted alkyl.

16. A compound according to claim 13 of the formula:

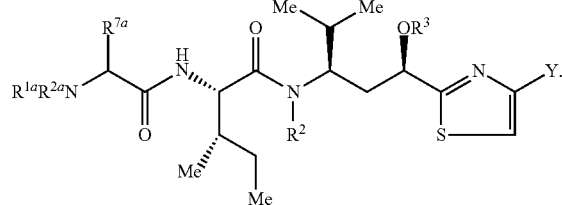

(VIII)

17. A compound according to claim 13 of the formula:

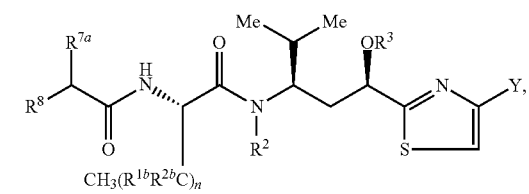

(V)

wherein $R^{1b}$ and $R^{2b}$ are independently selected from H and unsubstituted alkyl.

18. A compound according to claim 13 of the formula:

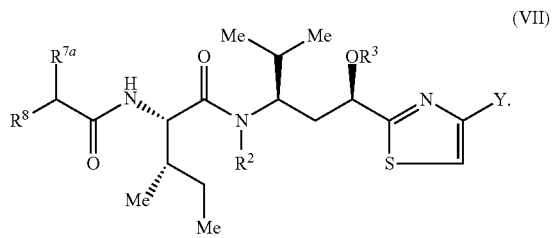

(VII)

19. The compound according to claim 13, which is selected from

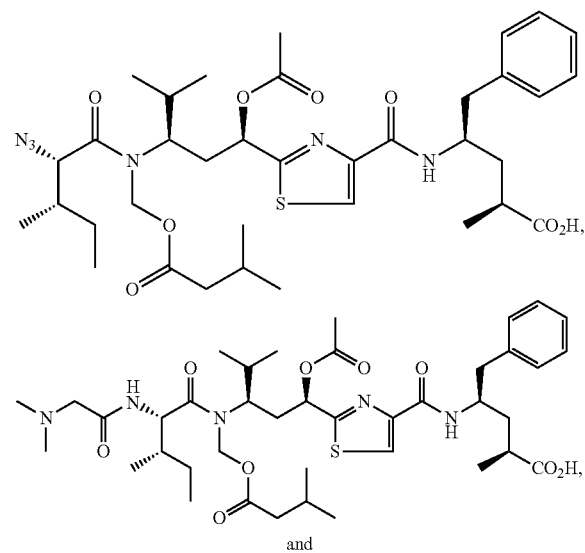

and

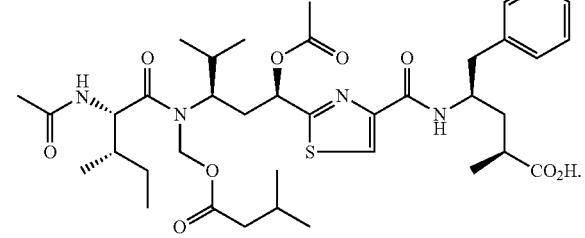

20. A pharmaceutical formulation comprising a compound according to claim 13 and a pharmaceutically acceptable diluent.

21. A method of treating colon cancer and cervix cancer in a subject, said method comprising administering to said subject a therapeutically effective amount of a compound according to claim 13.

22. A compound which is selected from

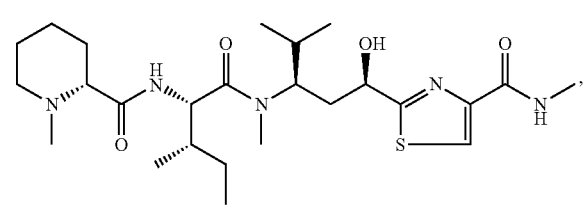

-continued
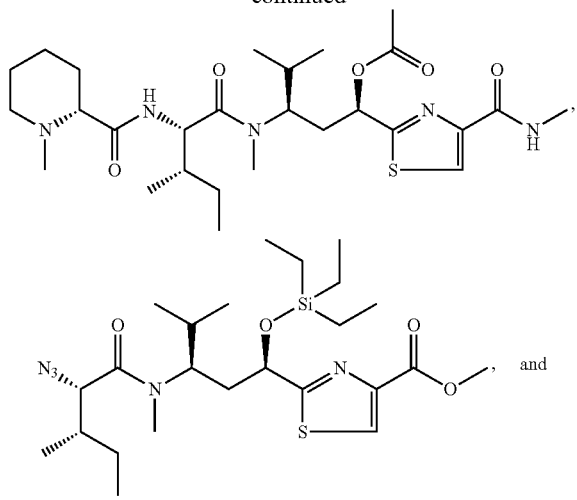
23. A pharmaceutical formulation comprising a compound according to claim 22 and a pharmaceutically acceptable diluent.
24. A method of treating colon cancer and cervix cancer in a subject, said method comprising administering to said subject a therapeutically effective amount of a compound according to claim 22.
* * * * *